(12) United States Patent
Montalban

(10) Patent No.: US 10,172,692 B2
(45) Date of Patent: Jan. 8, 2019

(54) RAPID PALATAL EXPANDER AND METHOD FOR THE MAKING THEREOF

(71) Applicant: VISOTTICA INDUSTRIE S.p.A, Susegana (TV) (IT)

(72) Inventor: Rinaldo Montalban, Venice (IT)

(73) Assignee: VISOTTICA INDUSTRIE S.P.A., Susegana (IT)

( * ) Notice: Subject to any disclaimer, the term of this patent is extended or adjusted under 35 U.S.C. 154(b) by 359 days.

(21) Appl. No.: 14/932,996

(22) Filed: Nov. 5, 2015

(65) Prior Publication Data
US 2016/0120622 A1    May 5, 2016

(30) Foreign Application Priority Data
Nov. 5, 2014    (IT) .............................. PD2014A0295

(51) Int. Cl.
*A61C 3/00*    (2006.01)
*A61C 7/10*    (2006.01)

(52) U.S. Cl.
CPC ...................... *A61C 7/10* (2013.01)

(58) Field of Classification Search
CPC ........................................................ A61C 7/10
USPC ................................................ 433/7, 10, 12
See application file for complete search history.

(56) References Cited

U.S. PATENT DOCUMENTS

| 3,921,294 A | * | 11/1975 | Wallshein | ................ | A61C 7/10 433/7 |
| 5,564,920 A | * | 10/1996 | Klapper | ................... | A61C 7/10 433/7 |
| 2004/0214126 A1 | * | 10/2004 | Forster | ..................... | A61C 7/10 433/7 |
| 2008/0171300 A1 | * | 7/2008 | Forster | ..................... | A61C 7/10 433/7 |
| 2015/0024333 A1 | * | 1/2015 | Montalban | ............... | A61C 7/10 433/7 |

FOREIGN PATENT DOCUMENTS

| DE | 199 45 444 | 4/2001 |
| EP | 0 919 207 | 6/1999 |
| EP | 0 962 193 | 12/1999 |
| JP | 2003 144460 | 5/2003 |

* cited by examiner

Primary Examiner — Yogesh Patel
Assistant Examiner — Gwen M Demosky
(74) Attorney, Agent, or Firm — Mark M. Friedman

(57) ABSTRACT

Rapid palatal expander provided with a first and a second main body actuatable to be moved along a longitudinal slide direction by an actuator element, and connected to at least one first and one second thread-like support arm intended to interact with opposite portions of a dental arch. The support arms comprise a transversely projecting portion, which is engaged in a shape relationship within an enlarged portion of a shaped seat obtained in the two main bodies. The shaped seat is extended on the external surface with an insertion opening of size at least equal to the transversely projecting portion.

10 Claims, 20 Drawing Sheets

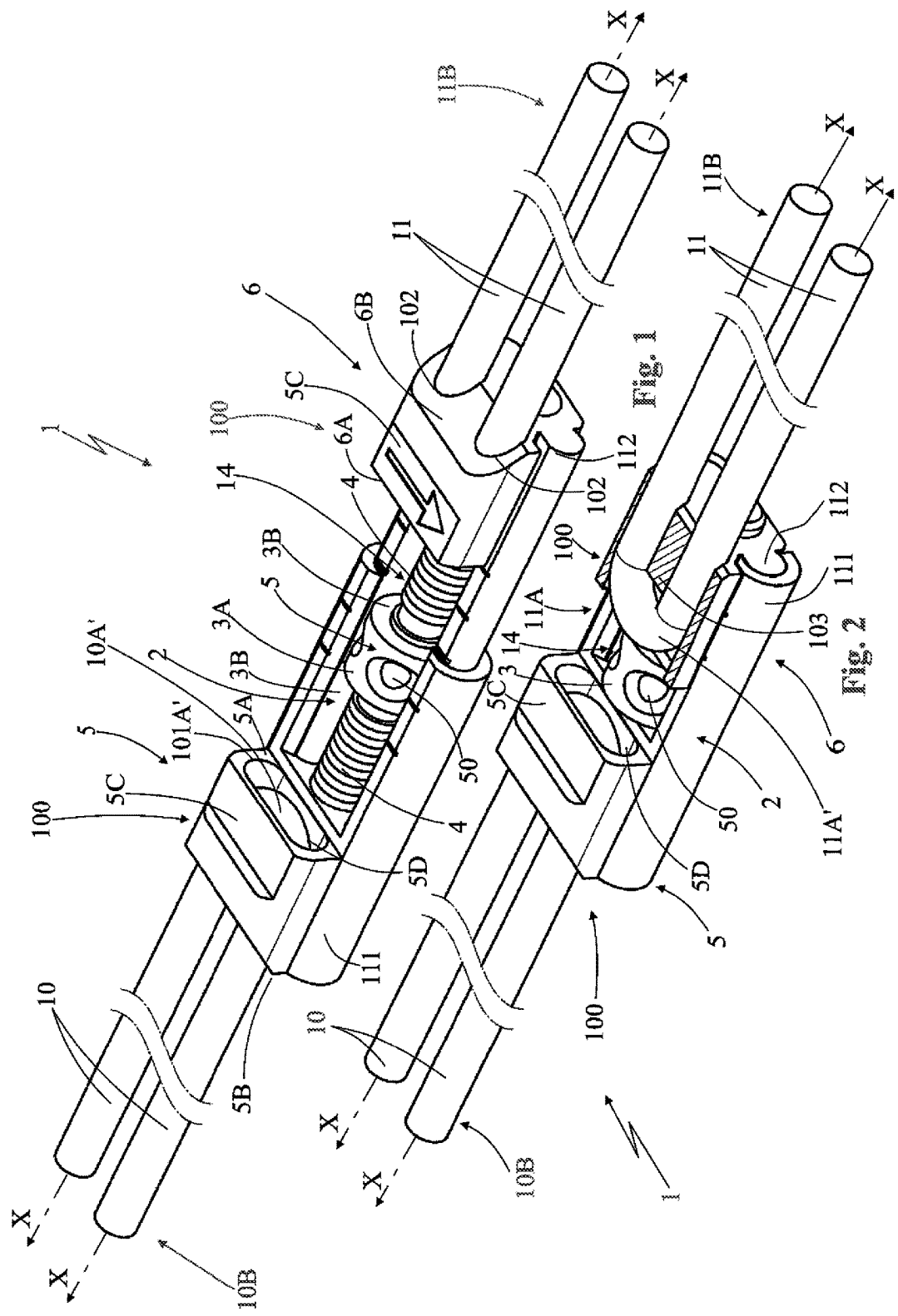

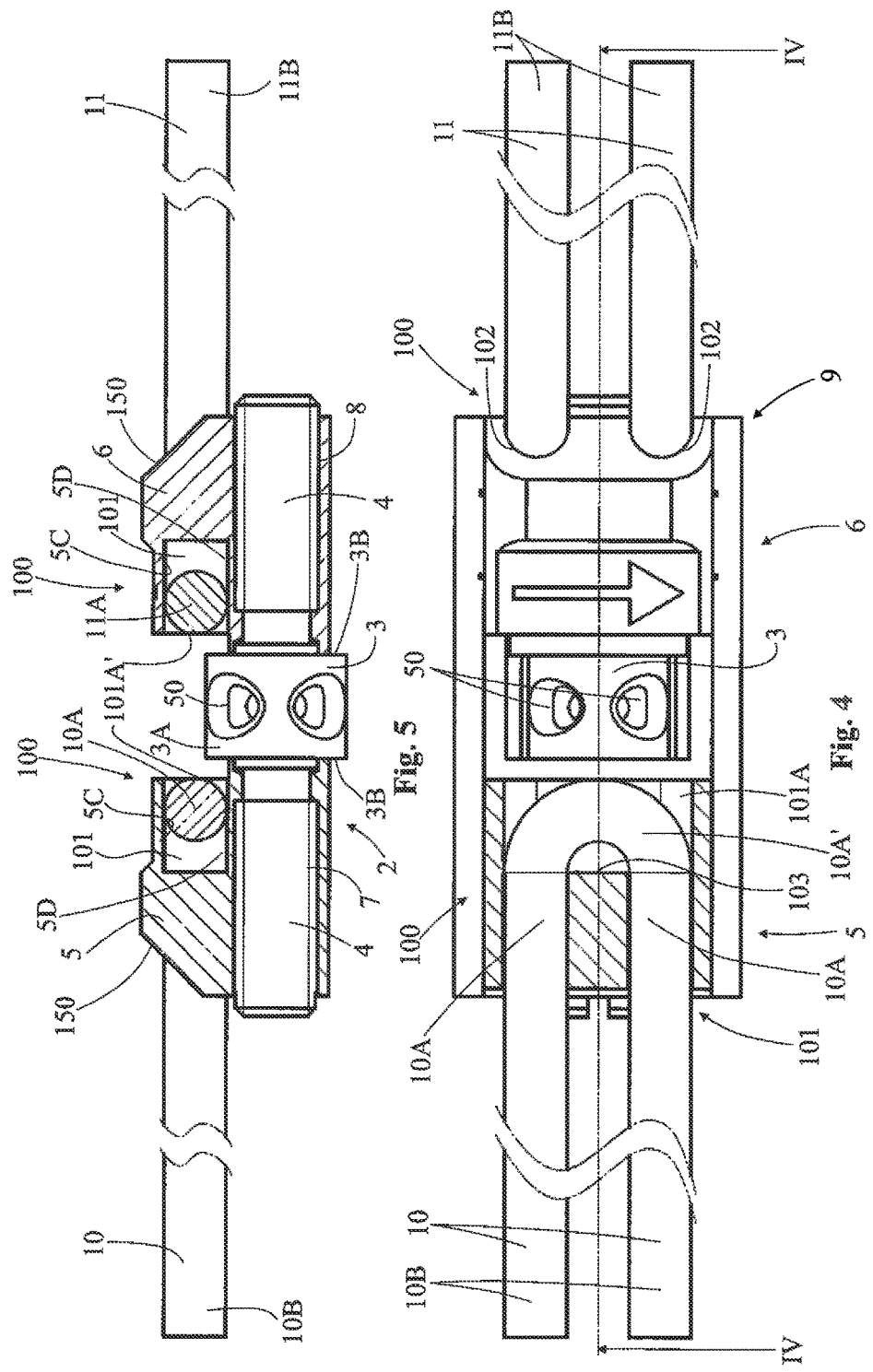

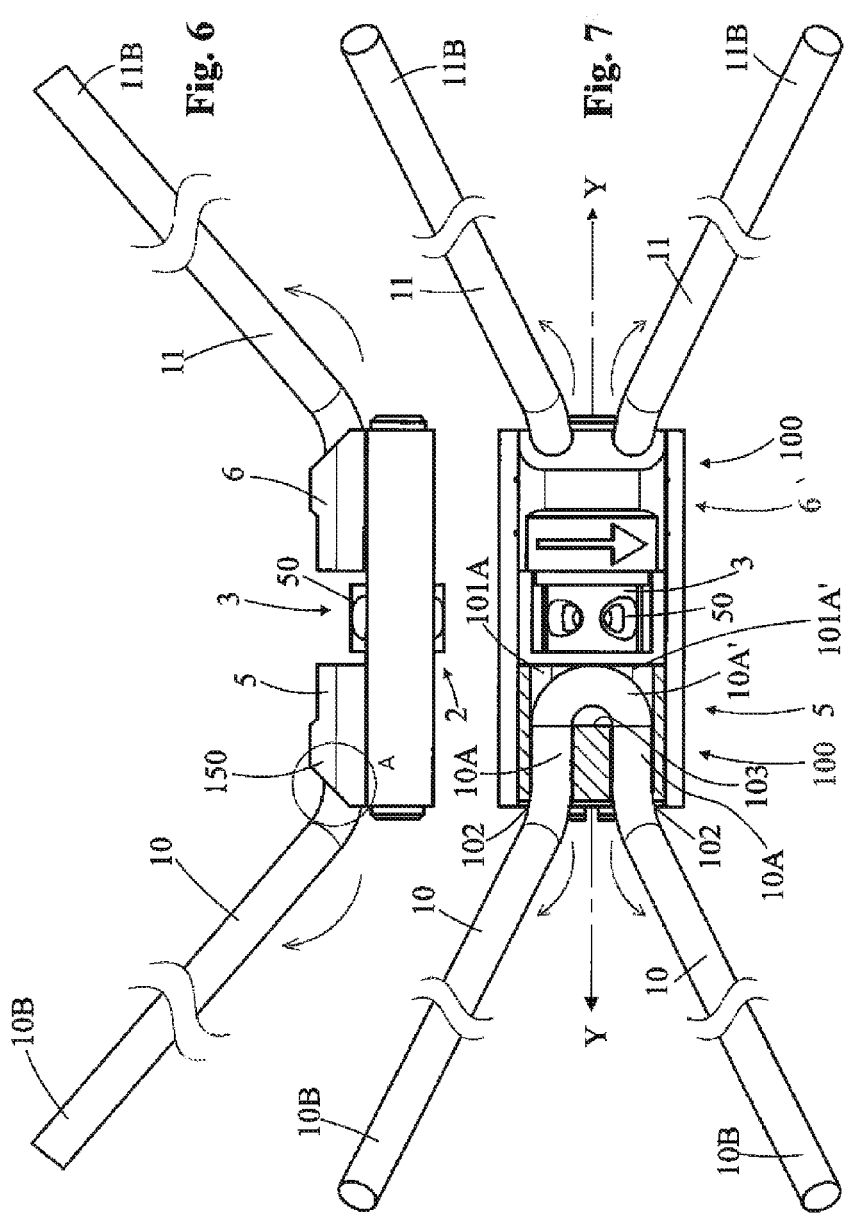

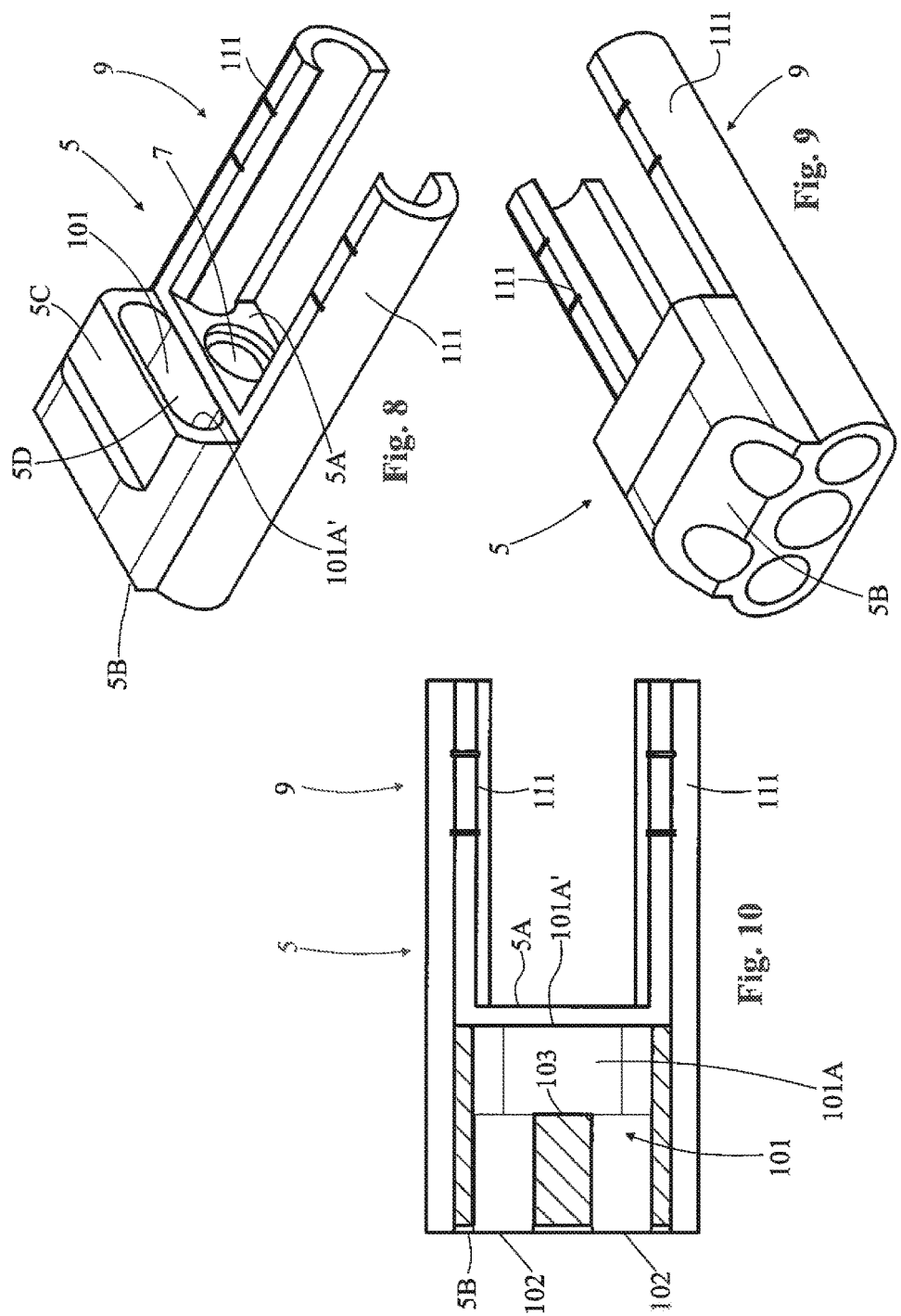

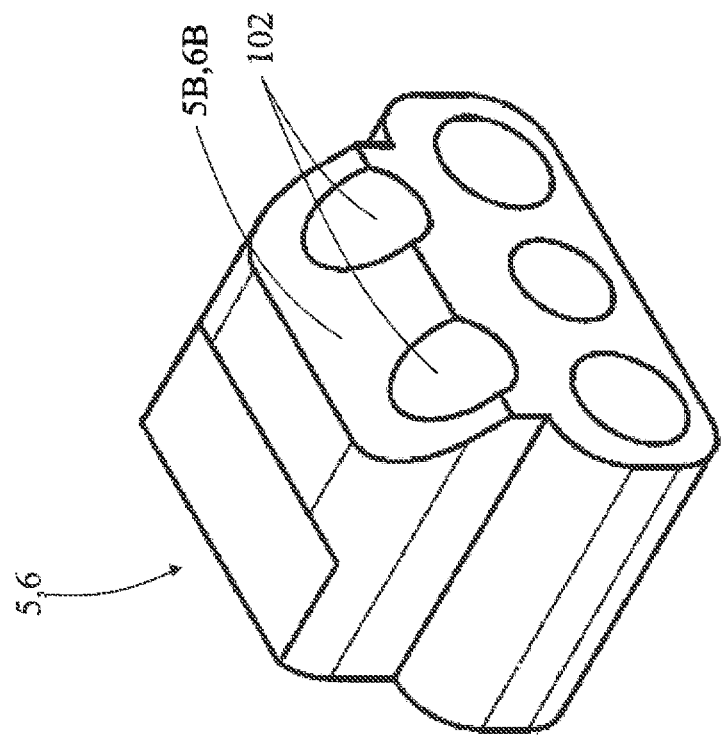
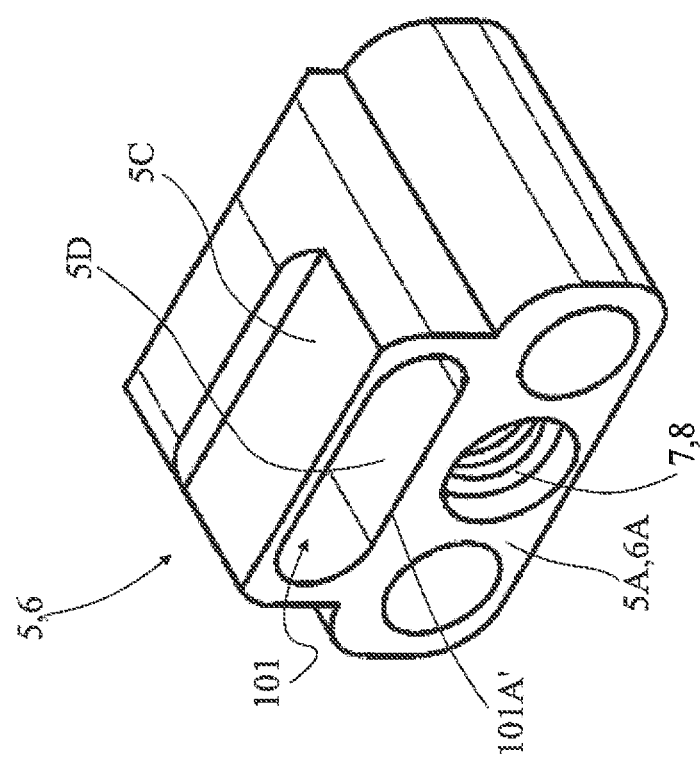
Fig. 16B
Fig. 16A

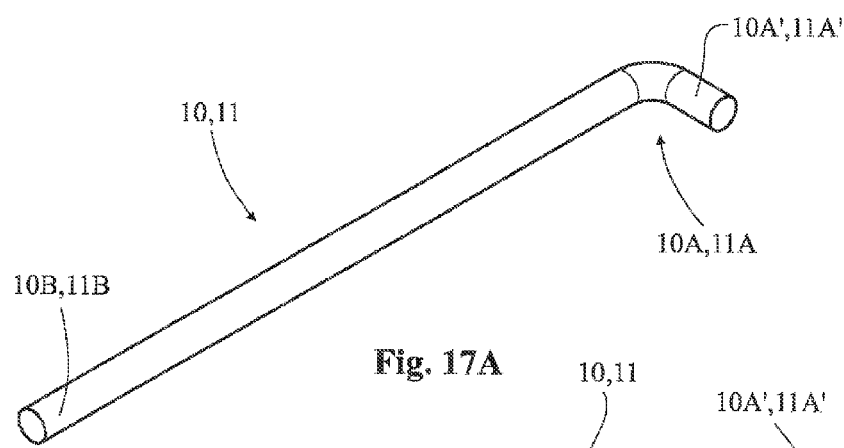
Fig. 17A
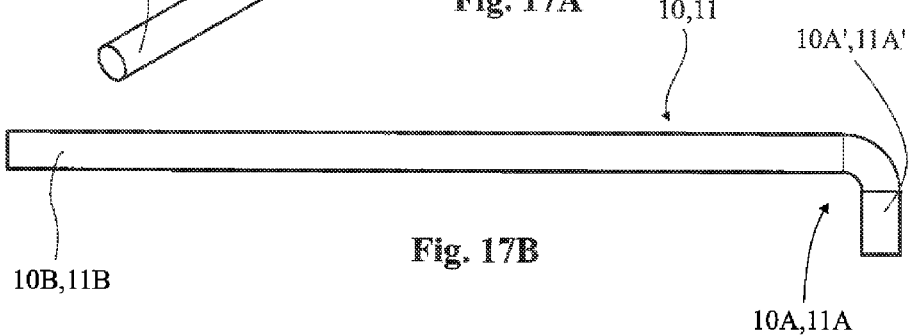
Fig. 17B
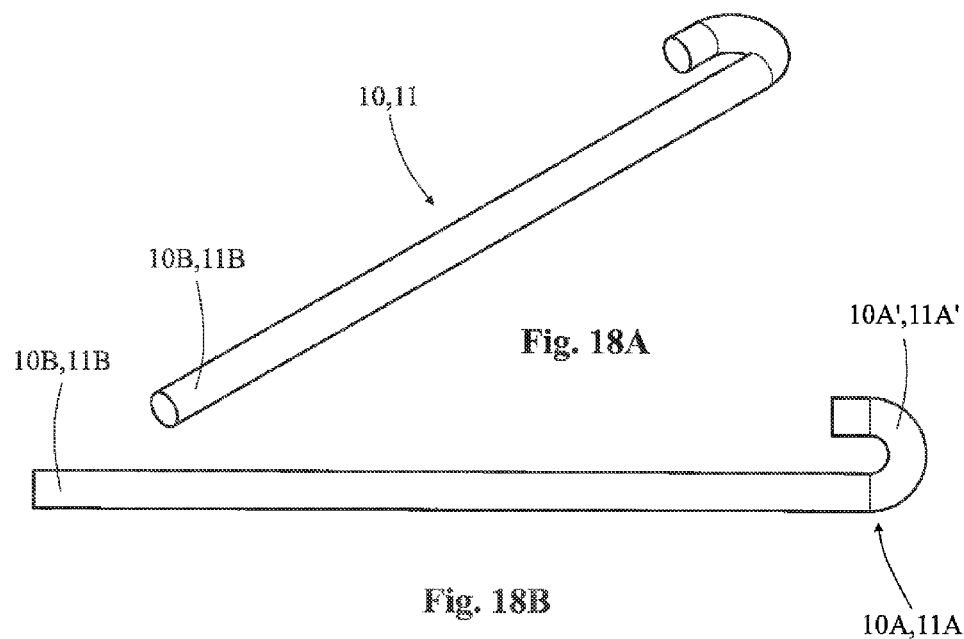
Fig. 18A
Fig. 18B

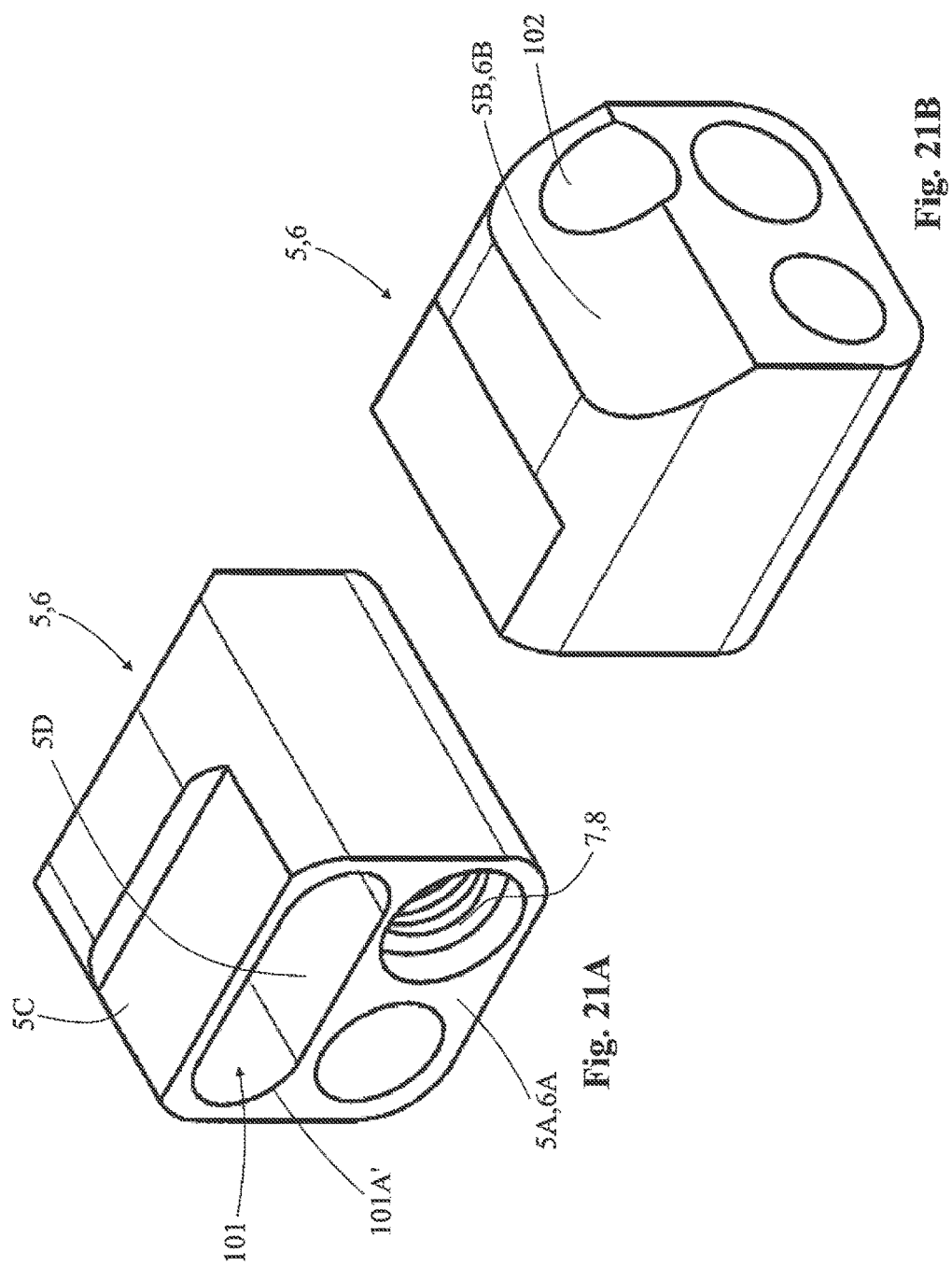

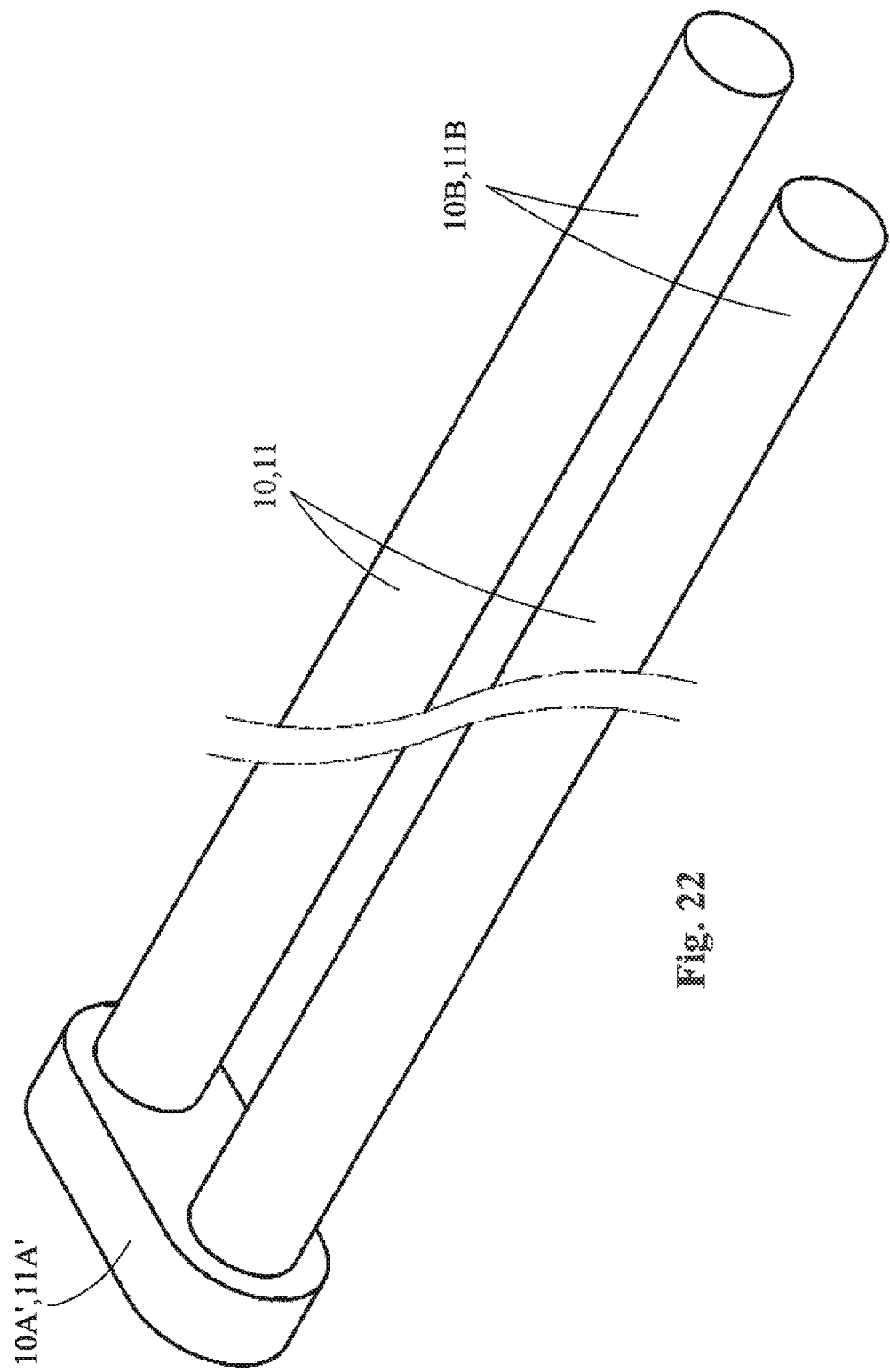

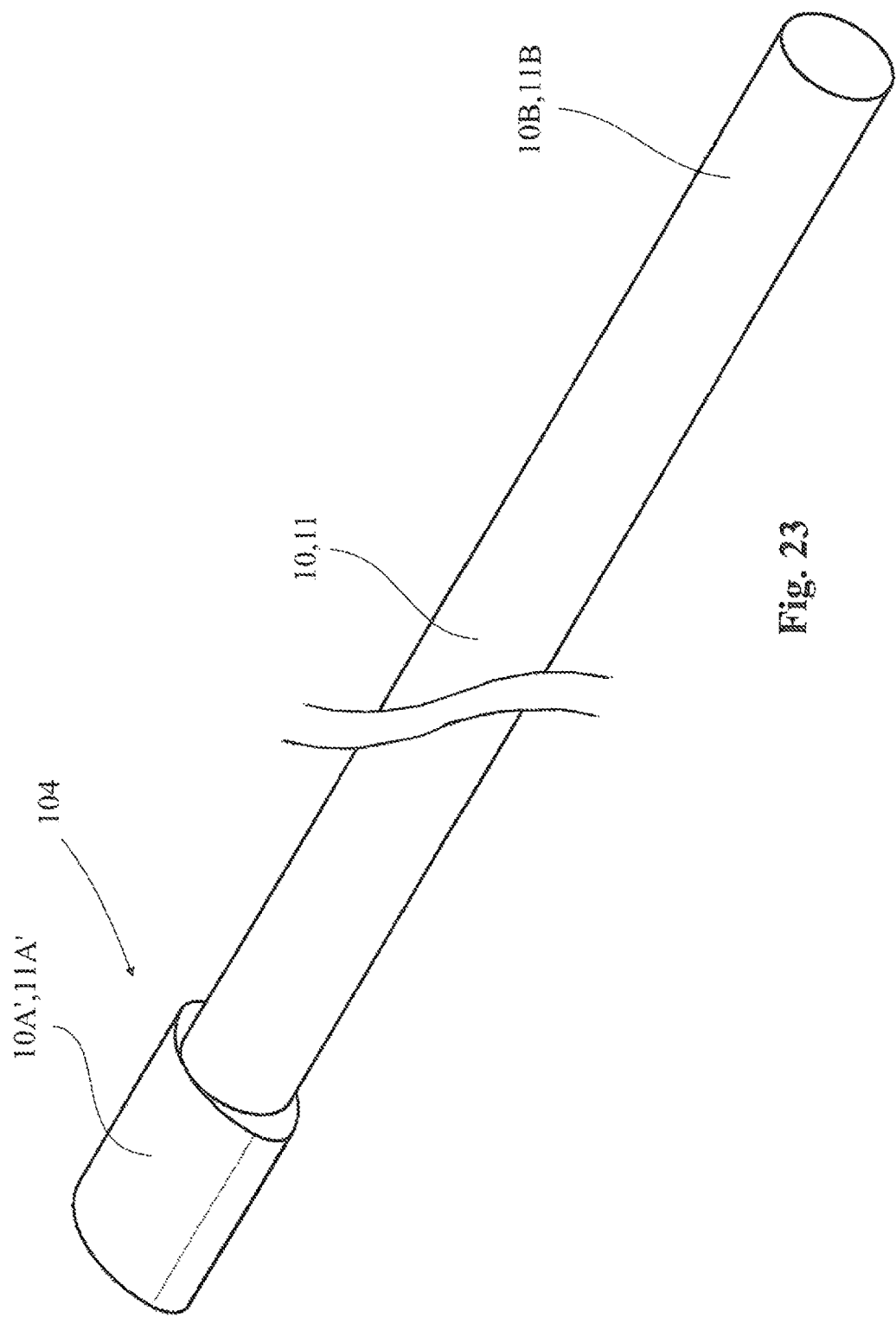

RAPID PALATAL EXPANDER AND METHOD FOR THE MAKING THEREOF

FIELD OF APPLICATION

The present invention regards a rapid palatal expander and a method for the making thereof, according to the preamble of the respective independent claims.

The present rapid palatal expander, otherwise termed palatal expander or spreader in the technical jargon, is advantageously intended for being employed in the field of orthodontics for treating cases of skeletal underdevelopment of the upper maxillary, especially for subjects in development age, before the end of puberty, when the median suture of the palate is not yet completely ossified.

It is an instrument that is applied in the mouth for a certain period of time and which causes the mechanical widening of the palate in a manner so as to create more space between the two rows of the upper dental arch.

The rapid palatal expander is therefore an orthodontics instruments and more generally a dental-maxillo-facial aid employable for the correction of a pathological condition of transverse growth deficit of the upper jaw, which can involve a poor dental occlusion, and can also have repercussions on phonesis, deglutition as well as respiration.

Therefore, the rapid palatal expander, object of the present invention, is inserted in the field of the orthodontic devices and the maxillo-facial devices.

STATE OF THE ART

As is known, the rapid palatal expanders (with ERP initials), currently employed in the field of orthodontics for the correction of the transverse growth deficit of the upper jaw, provide for moving apart two bodies that are mechanically associated with at least two opposite portions of the dental arch, through the actuation of a screw engaged with the same bodies and usually of the type with double and opposite thread.

More in detail, a conventional palatal expander usually comprises:

two main bodies mechanically connected to two or more palate arms (or support arms), which are extended in opposite directions, and which are intended to interact, by means of fixing means (e.g. constituted by molar or premolar bands) or other mechanical elements, with corresponding opposite portions of the dental arch;

an elongated twin-screw actuator element provided with an actuation head with cylindrical form arranged in a median position thereof, and with two stems with threads with opposite senses obtained, such stems extended aligned in opposite directions, starting from the actuation head, until they are engaged in threaded seats of the two main bodies; the actuation head is peripherally provided with holes for the insertion of a tool (a key) adapted to allow the rotation of the twin-screw element for the mutual moving apart of the two main bodies and hence of the molar bands that act on the arch;

one or two guide pins, which are slidably inserted inside corresponding holes obtained in the two main bodies, in order to guide the translation of the latter following the driving in rotation of the twin-screw element.

Therefore, the driving of the twin-screw actuator element (obtained by rotating the head, by means of the suitable key, one-quarter of a revolution) regulates the mutual moving apart of the two main bodies and consequently the greater or lesser pressure exerted by the palate arms on the respective arch portions.

The palate arms are metal thread-like elements with thickness usually on the order of a millimeter, which transmit the widening movements of the two bodies of the expander to the palate arch. For such purpose, they terminate with means for fixing to the tooth, usually formed by bands or closed rings wound around the tooth, to which they are fixed by means of cementation.

The arms are generally directly fixed to the metal bands wound on the teeth by means of welding. Otherwise, they can be employed in tubes provided on portions projecting from the bands in order to transmit twisting to the tooth as well. Often, the arms act on the teeth through a molar or premolar band, or even through a metal arch usually shaped starting from a band and having a plurality of undulations aimed to follow the internal profile of the dental arch to be widened.

In any case, the thread-like (o rod-like) arms must be modeled with permanent deformations that place them in the correct position for transmitting the desired expansion action to the teeth.

They must have particular mechanical characteristics that confer them a sufficient rigidity for the mechanical transmission of the expansion forces, but also a flexibility sufficient for allowing the modeling thereof during the application of the expander, so as to allow connecting the bodies of the expander to the molar bands (or other connection elements) in the correct expansion direction.

The rapid palatal expanders currently present on the market have drawbacks connected with the fixing of the arms to the two mutually movable bodies of the rapid palatal expander.

In particular, the expander must be modeled on the work model that reproduces the teeth of the patient (and hence in accordance with the anatomy of the patient), and it must also be made according to the correction that is desired to impart to the arches. For such purpose, the prosthodontist must carry out a work of modeling the rapid palatal expander device by permanently deforming the aforesaid support arms with considerable effort and in different directions.

In order to carry out such modeling, the prosthodontist usually uses dedicated instruments such as the bender capable of exerting considerable stress on the same wires, which will mainly be unloaded at the zone of their connection with the two main bodies of the expander, considerably straining the relative fixing.

Therefore, not only is the intrinsic strength of the wire of the arms of fundamental importance, but also a correct geometry and a correct joining of the arms to the bodies of the expander is essential.

Generally, the support arms are components initially separated from the two main bodies and are joined to the latter by means of joining via laser welding (direct or spot) or through other joints of known type.

Advantageously, the main bodies have suitable seats, in which portions of the arms are housed, thus increasing the seal of the joint.

The patents U.S. Pat. No. 7,837,465, U.S. Pat. No. 8,821,156 and US 2004/0214126 disclose several solutions of palatal expanders of the above-described known type, in which, in particular, the arms are housed in elongated seats with open cylindrical groove shape, and are fixed therein by means of long weld beads.

These joints of the arms to the bodies of the expanders of known type do not offer sufficient mechanical seal assurances, and the prosthodontist must pay extreme attention in handling the arms in order to prevent a separation thereof from the bodies, which up to now has proven to be a rather frequent drawback.

More in detail, during modeling, as stated, various bends are executed for positioning the bands and the bodies of the expander in the correct mutual position. For such purpose, the wires of the arms are deformed multiple times and in multiple spatial directions, creating stresses also of torsional type which are mainly unloaded on the weld zone, since the arms and the relative seats do not have particular expedients for being to oppose such torsional stresses, being in fact obtained with cylindrical forms that are axially coupled together.

Therefore, in accordance with the palatal expanders of known type and in particular in accordance with the solutions described in the patents U.S. Pat. No. 7,837,465, U.S. Pat. No. 8,821,156 and US 2004/0214126, even if each arm is inserted for a section thereof within a respective counter-shaped seat obtained on a corresponding main body, in reality the only item that ensures the seal with the relative rotations between arm and body, due to the various bends of the wire, is the weld existing between the same arm and the main body.

Therefore, the rapid palatal expanders of known type described above have the drawback of unsuitable joints between arms and bodies—unsuitable for resisting the torsional stresses exerted by the prosthodontist during the modeling operations.

In order to at least partly overcome this drawback, i.e. in order to more greatly ensure the seal of the weld in particular with respect to the torsional stresses, very large weld beads are operated. However, such circumstance causes the non-negligible drawback of a lengthening of the production times, which of course also negatively affects the final costs of the manufactured item. Further drawback of such large welds clearly also lies in the poor aesthetics of expanders with evident weld beads, which give the prosthodontist the impression of a very artisanal manufactured product design.

In order to overcome the drawbacks of the above-described rapid palatal expanders, expanders have also been developed that have the support arms made integrally with the main bodies.

One rapid palatal expander embodiment solution of the above-described known type is reported in the patent WO 2012042547.

If on one hand the expanders with the arms integral with the relative main bodies avoid the abovementioned criticalities connected with the welds, on the other hand they have the drawback of requiring a component shaped with a rather complex form, unsuitable for being used in all the geometries of palatal expanders, such as in the expanders with telescopic bodies described in the patent application US 2013/943830.

A further drawback of the rapid palatal expanders having the arms integral with the relative main bodies lies in the fact that the support arms and the main bodies meet different technical characteristics, which often lead them to being made of materials that are different from each other. In particular, the arms—since they have to be bent—must also ensure good deformability characteristics, while the main bodies—having particular shapes—are generally obtained by processing with machine tools so that they must ensure good processability characteristics. The two needs are hard to reconcile with the use of a single material for the arms and bodies.

Also known from the patents EP 0962193 and DE 19945444 are palatal expanders whose main bodies are obtained by means of injection of plastic material, in which the corresponding support arms are partially embedded. In this manner, the main bodies incorporate at their interior an internal section of the corresponding support arms, which exit from the main bodies only with corresponding external sections adapted to act on the teeth of the user.

One drawback of the palatal expanders described in the patents EP 0962193 and DE 19945444 lies in the fact that they require costly and complex processes for the making thereof, due in particular to the need to make the main bodies by means of injection molding.

PRESENTATION OF THE INVENTION

In this situation, the problem underlying the present invention is to eliminate the drawbacks of the abovementioned prior art, by providing a rapid palatal expander which has arms for transmitting the action of expansion on the dental arches, with improved mechanical characteristics.

A further object of the present finding is to provide a rapid palatal expander whose arms are not subjected to separations from the relative main bodies during the modeling operations carried out by the prosthodontist.

A further object of the present finding is to provide a rapid palatal expander whose arms are optimized with regard to their mechanical characteristics, independent of the mechanical and production requirements of the main bodies.

A further object of the present finding is to provide a rapid palatal expander which is structurally simple and entirely reliable in operation.

A further object of the present finding is to provide a rapid palatal expander which is inexpensive to make.

A further object of the present finding is to provide a method for making a rapid palatal expander which is easy to execute and which improves the fixing of the arms to the relative main bodies.

These objects and still others will all be attained by the rapid palatal expander, object of the present invention, which comprises one first and one second main body; an actuator element mechanically engaged with the first and second main body and actuatable to move the latter relative to each other along a longitudinal slide direction; one first and one second support arm, provided with a thread-like extension along an axis X, mechanically fixed at a connection portion thereof to the first and second main body by means of respective fixing means, and susceptible of imparting corrective actions on opposite dental arches of a patient through a terminal portion thereof.

According to the idea underlying present invention, the rapid palatal expander is characterized in that: the connection portion of the first and second support arm comprises a transversely projecting portion, cylindrically asymmetrical with respect to the extension axis X of the first and second support arm; the first and the second main body comprise at least one shaped seat provided with at least one enlarged portion counter-shaped with respect to the transversely projecting portion and engaged by the latter in a shape relationship, the enlarged portion of the shaped seat being extended with at least one insertion opening on the external surface of the first and second main body.

BRIEF DESCRIPTION OF THE DRAWINGS

The technical characteristics of the finding, according to the aforesaid objects, can be clearly seen in the contents of the below-reported claims and the advantages thereof will be more evident from the following detailed description, made with reference to the enclosed drawings, which represent several merely exemplifying and non-limiting embodiments thereof, in which:

FIG. 1 shows a general perspective view of one embodiment of the rapid palatal expander according to the present invention in open condition;

FIG. 2 shows a perspective view of the rapid palatal expander of FIG. 1 in closed condition and with a sectional part of a main body removed in order to better illustrate other parts;

FIG. 4 shows a top view of the rapid palatal expander of FIG. 2;

FIG. 5 shows a sectional side view of the expander of FIG. 4, carried out along the line IV-IV of FIG. 4;

FIG. 6 shows a side view of the expander of FIG. 2, on which a first deformation of the support arms has been carried out in the direction indicated by the arrows;

FIG. 7 shows a second top view of the rapid palatal expander of FIG. 6, on which also a second deformation of the support arms has been carried out in the direction indicated by the arrows;

FIG. 8 shows a perspective view of a detail of the palatal expander of FIG. 1 relative to a main body with its front face visible;

FIG. 9 shows a perspective view of the main body of FIG. 8 with its rear face visible;

FIG. 10 shows only the sectional main body of FIG. 8 in a top view;

FIGS. 16A and 16B show two different perspective views of an enlarged detail of the palatal expander of FIG. 15 relative to a main body;

FIGS. 17A and 17B show a detail of a variant of the palatal expander relative to a support arm in accordance with a possible embodiment with L-shaped termination respectively in a perspective view and in a top view;

FIGS. 18A and 18B show a detail of a variant of the palatal expander relative to a support arm in accordance with one possible embodiment with J-shaped termination, respectively in a perspective view and in a top view;

FIGS. 21A and 21B show two different perspective views of an enlarged detail of a variant embodiment of the palatal expander relative to a main body with screw and only one guide pin and with a shaped seat provided for housing a single L-shaped support body according to the embodiment variant of FIGS. 17A and 17B and hence with a single passage opening;

FIG. 22 shows a perspective view of a detail of a variant of the palatal expander relative to two parallel support arms held together by a transverse joint portion;

FIG. 23 shows a perspective view of a detail of a variant of the palatal expander relative to a support arm in accordance with one possible embodiment, with enlarged head termination;

DETAILED DESCRIPTION OF A PREFERRED EMBODIMENT

Figure 3:
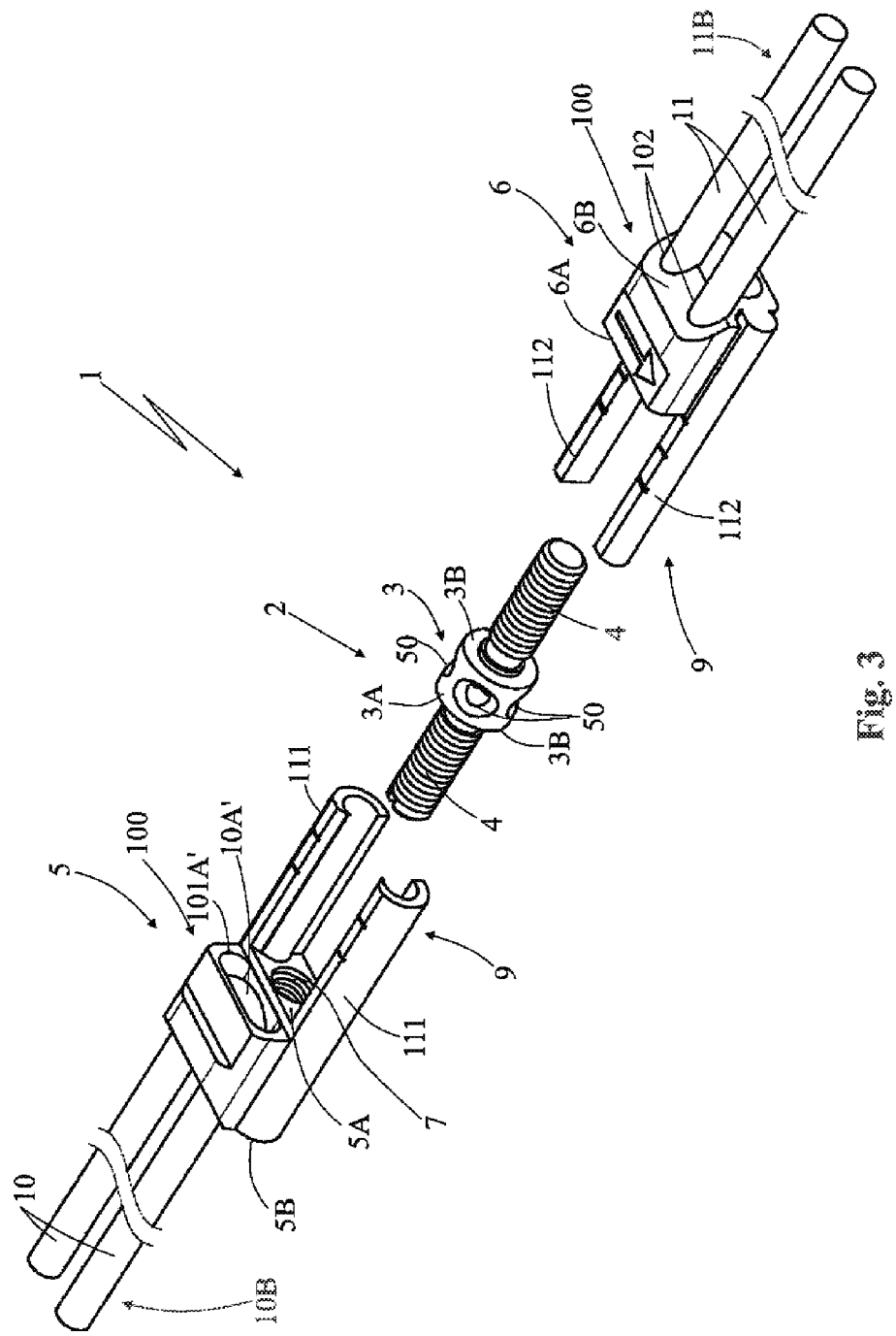
FIG. 3 shows a perspective exploded view of the rapid palatal expander of FIG. 1.
Figure 11:
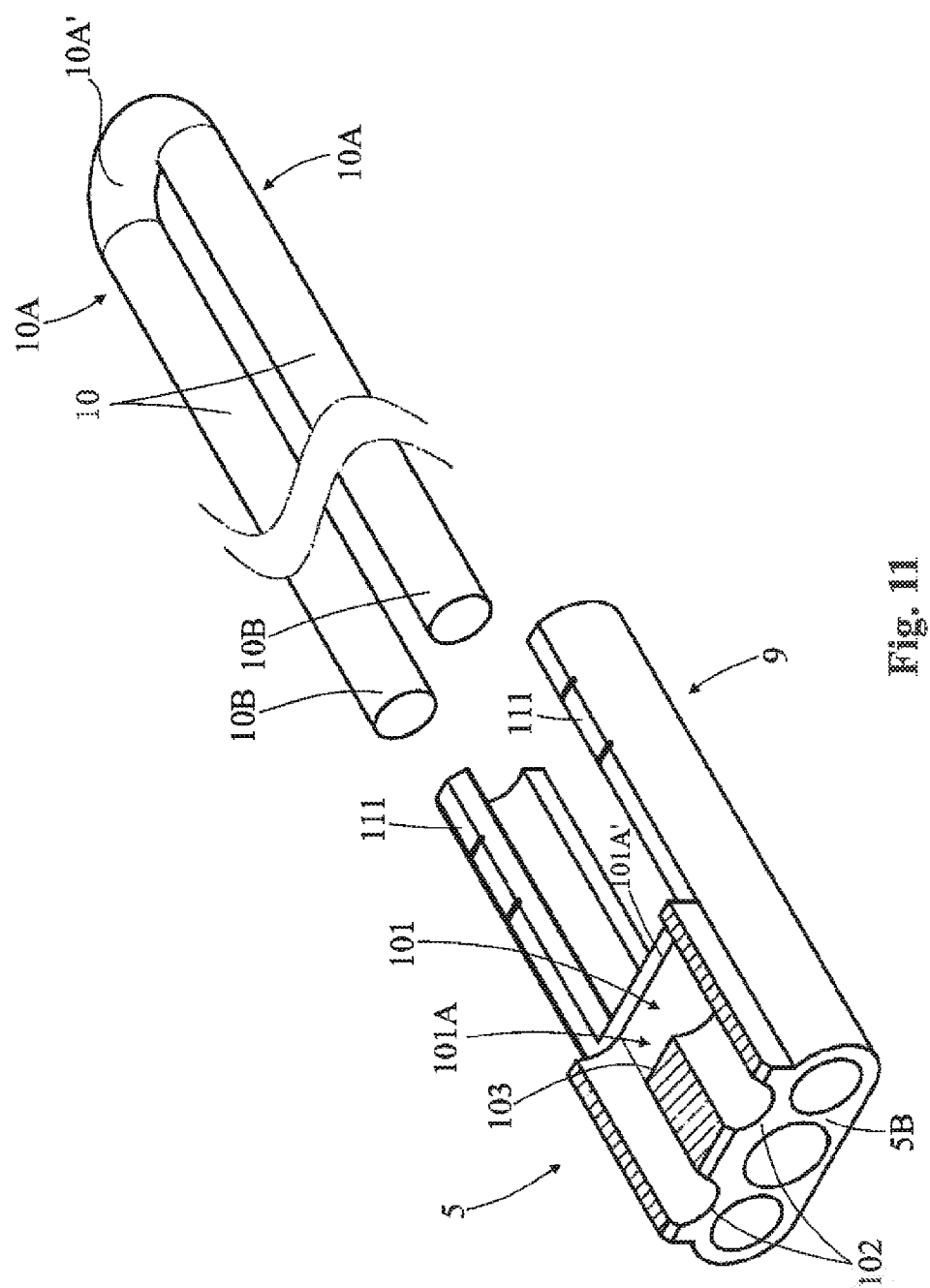
FIG. 11 shows the sectional main body of FIG. 8 in a perspective view with, side-by-side in a non-assembled manner, two support arms joined together by a U-shaped connection portion.
Figure 12:
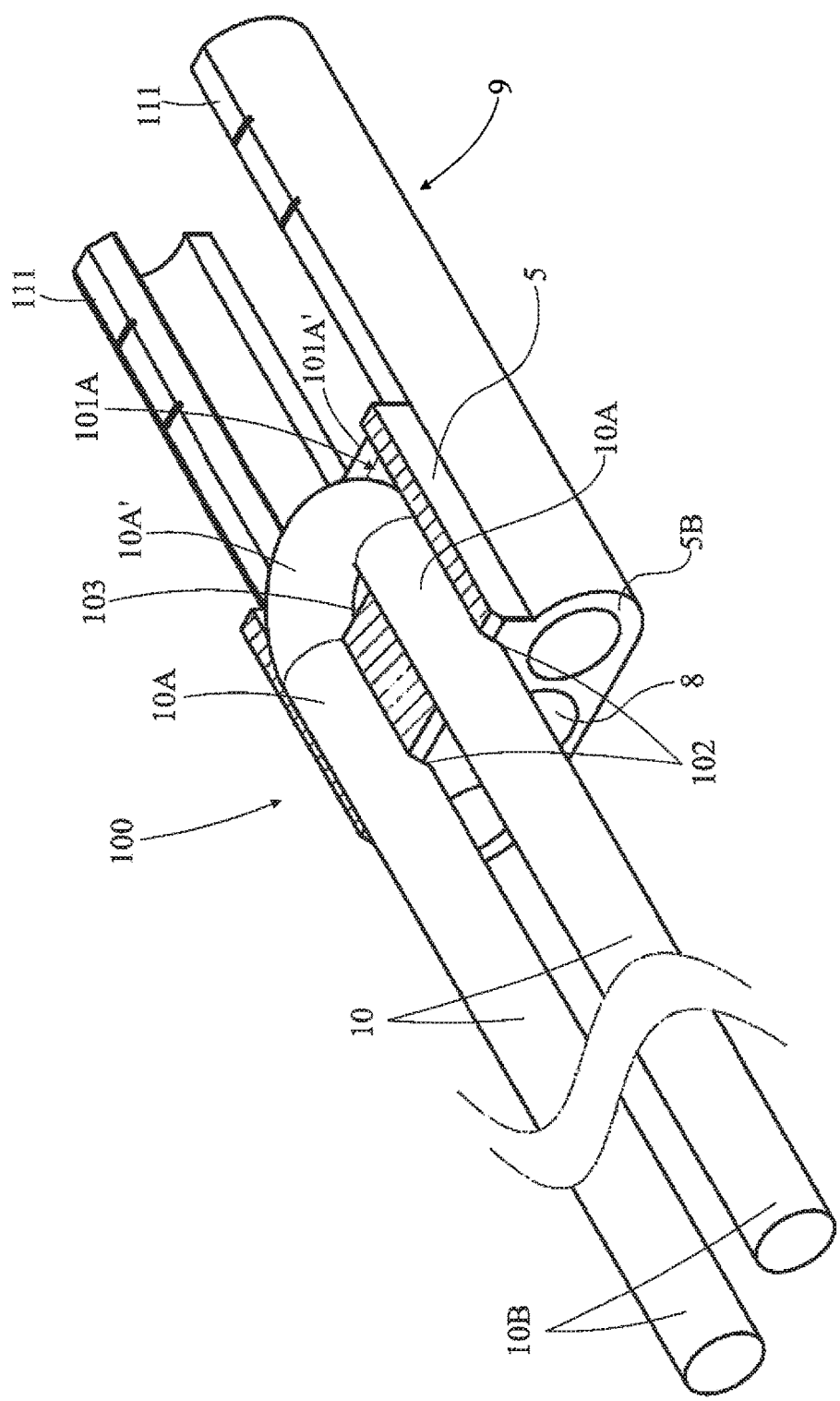
FIG. 12 shows a perspective view of the sectional main body of FIG. 11 with the two support arms housed in a provided shaped seat of the same main body.

With reference to the enclosed drawings, reference number 1 overall indicates a rapid palatal expander, object of the present invention.

The rapid palatal expander 1, according to the present invention, is intended to be employed in a per se conventional manner in the field of orthodontics for the pathological correction of an underdevelopment of the upper maxillary, as already indicated above in the description of the application field of the present finding.

In accordance with its known general functioning principle, the expander 1 comprises two main bodies, indicated hereinbelow as first main body 5 and as second main body 6, and at least two rigid support arms, indicated hereinbelow as first support arm 10 and as second support arm 11. The support arms 10, 11 are mechanically fixed at a connection portion 10A, 11A thereof to the first and second main body 5, 6, are extended in substantially opposite directions and are intended to interact against corresponding opposite portions of a dental arch (not illustrated) in order to impart opportune corrective actions, through a terminal portion 10B, 11B thereof.

More in detail, anchorage elements 100 are provided for fixing the connection portions 10A, 11A of the arms 10, 11 to the two main bodies 5, 6, preventing the unthreading thereof, which will be specified in detail hereinbelow.

The terminal portions 10B, 11B of the same arms 10, 11 are susceptible of acting on the dental arches by means of mechanical members per se known to the man skilled in the art and for this reason not described and illustrated in detail, such as teeth anchorage bands (molar bands, premolar bands) and/or other mechanical transmission elements, such as curved portions shaped according to the internal profile of the neck of the teeth that compose the dental arch section, on which the correction operation will take place.

In accordance with most of the embodiments illustrated in the enclosed drawings, two support arms 10 or 11 are usually provided for each main body 5, 6. Indeed, in accordance with the correction to be made, it is necessary to operate on a more or less wide area of the dental arches, hence correspondingly with one or two support arms 10, 11.

The latter are provided with a thread-like or rod-like extension along an extension axis X and are made of a metal material or of a metal alloy, usually with a thickness of about one millimeter. The thread-like extension of the wire preferably occurs starting from a circular cross section.

The expander 1 also comprises an actuator element 2 mechanically engaged with aforesaid first and second main body 5, 6 and manually actuatable for moving the latter relative to each other along a longitudinal slide direction Y, in order to vary over time the expansion force exerted by the arms 10, 11 on the dental arches.

Such actuator element 2 is for example provided with a central actuation head 3, i.e. placed in a substantially median position with respect to the its longitudinal extension, and with two stems 4 which are extended aligned with each other along such longitudinal direction Y, in opposite directions starting from the aforesaid actuation head 3. The two stems 4 are provided with two threads oriented in opposite directions such that there is a simultaneous screwing and unscrewing for both stems 4 with respect to corresponding nuts on which they are engaged, as described hereinbelow.

The head 3 has a substantially cylindrical peripheral surface 3A which is extended in a coaxial manner with respect to the longitudinal direction Y. Such peripheral surface 3A is delimited in the longitudinal direction Y by two lateral surfaces 3B transverse to the direction Y, from which the stems 4 are extended in opposite directions.

According to the idea underlying present invention, the connection portion 10A, 11A of the first and second support arm 10, 11 comprises a transversely projecting portion 10A', 11A', cylindrically asymmetrical with respect to the axis of the thread-like extension of the same first and second support arm 10, 11.

In addition, the two main bodies 5, 6 comprise at least one shaped seat 101 provided with at least one enlarged portion 101A counter-shaped with respect to the transversely projecting portion 10A', 11A' and engaged by the latter in a shape relationship in order to prevent the relative rotation thereof around the axis of the thread-like extension of the respective first and second support arm 10, 11.

The enlarged portion 101A of the shaped seat 101 is extended with at least one insertion opening 101A' on the external surface of the first and second main body 5, 6 in order to allow the introduction of the transversely projecting portion 10A', 11A' of the corresponding support arm 10, 11.

Due to the above-described coupling, each support arm 10, 11 is firmly fixed to the relative main body 5, 6, and with its transversely projecting portion 10A', 11A' in abutment against the enlarged portion 101A of the shaped seat 101 it is able to unload the torsional moments to which it is subjected, e.g. during the modeling carried out by the prosthodontist. Indeed, the metal wire composing each support arm 10, 11, in accordance with the present invention, can no longer rotate around its axis X in the seat 101, as instead occurs in the solutions of expanders of known type, which consequently unload strong shear stresses on the provided welds.

Advantageously, the insertion opening 101A' of the enlarged portion 101A of the shaped seat 101 of each main body 5, 6 has, at the external surface of the respective main body 5, 6, size greater than or equal to the cross section of the transversely projecting portion 10A', 11A' engaged in the corresponding enlarged portion 101A, in a manner so as to allow (while making the expander 1) the transversely projecting portion 10A', 11A' to be inserted in the enlarged portion 101A of the corresponding shaped seat 101 through the corresponding insertion opening 101A'.

In particular, by cross section of the transversely projecting portion 10A', 11A', it is intended the maximum surface area delimited by the external perimeter of the section of the transversely projecting portion 10A', 11A' executed on a plane transverse to the longitudinal slide direction Y.

As stated, the transversely projecting portion 10A', 11A' is cylindrically asymmetrical with respect to the axis of the thread-like extension X of the same first and second support arm 10, 11, by such expression it being intended the presence of at least one portion 10A', 11A' with eccentric shape projecting from the circular section of the wire which prevents the rotation of the latter in the corresponding shaped seat 101, coming to abut against the aforesaid enlarged portion 101A.

The enlarged portion 101A of the shaped seat 101 encloses the transversely projecting portion 10A', 11A' of the connection portion 10A, 11A of said first and second support arm 10, 11 by an arc around the extension axis X of the latter sufficient for preventing the rotation of the transversely projecting portion 10A', 11A' in the enlarged portion 101A.

Preferably, at least two opposite walls of the seat are always present, in order to prevent the aforesaid rotation.

Advantageously in accordance with the illustrated embodiments, at least one upper wall 5C and at least one lower wall 5D, opposite each other, are always present. Such walls delimit two mirrored impressions of the enlarged portion 101A, and they prevent the rotation within the transversely projecting portion 10A', 11A' of said first and second support arm 10, 11.

The first main body 5 and the second main body 6 are provided with corresponding first front face 5A and second front face 6A, which are arranged parallel to and facing each other.

The two bodies 5 and 6 are also provided with a first rear face 5B and a second rear face 6B oriented in directions opposite each other as well as opposite with respect to the orientation of the corresponding first front face 5A and second front face 6A provided on the same main bodies 5, 6.

On such front faces 5A, 6A, respective nuts 7 and 8 are obtained that are aligned with each other, and each engaged by one of the two threaded stems 4 of the actuator element 2.

As can be observed in particular in FIGS. 5 and 7 (indicated in the latter figure with a circle), the rear faces 5B and 6B are provided with a wall 150 tilted substantially 45 degrees, which facilitates the bent modeling of the support arms 10, 11.

Guide means 9 are then preferably provided for guiding the simultaneous movement of the two main bodies 5, 6 in an advancement direction thereof that coincides with the longitudinal extension direction Y of the actuator element 2. The two main bodies 5, 6, being engaged with the stems 4 with opposite threads of same actuator element 2, are moved, following the rotation of the actuation head 3, closer or further apart and always in a synchronized manner in the same direction Y but in opposite directions.

More in detail, the guide means 9, following the rotation of the actuation head 3 in a first rotation direction thereof, facilitate the guided movement of the two main bodies 5, 6 for at least one adjustment travel, from at least one collected position, in which the main bodies 5, 6 are brought close to each other, to at least one expanded position, in which the main bodies 5, 6 are spaced from each other.

In operation, once the rapid palatal expander 1 is installed in the patient's mouth, with the bands engaged on the teeth in order to transmit thereto, through the arms 10, 11, the thrust pressure of the main bodies 5, 6 held spaced by the action of the actuator 2, one proceeds day-by-day to support the enlargement movement set by the actuator element 2 by means of the arms 10, 11 on the rows of teeth of the dental arch of the patient, by rotating the actuation head 3 of the actuator 2 a predefined angle, usually an angle of 90 degrees each day or a multiple of 90 degrees each day.

Advantageously, in order to prevent the rotation of the actuation head 3 of the actuator element 2 in the second rotation direction opposite the first, i.e. in the direction aimed to reapproach the two main bodies 5, 6, anti-rotation means can be provided.

The abovementioned guide means 9 can be obtained in accordance with different embodiments.

In accordance with one possible embodiment illustrated in FIGS. 1-14, 26, 27, the guide means 9 comprise a first pair of rods 111, which are rigidly fixed to the first main body 5, and in particular are integrally obtained with the latter, and are extended parallel to each other towards the second main body 6 starting from the first front face 5A, and a second pair of rods 112, which are in turn rigidly fixed to the second main body 6, and in particular they are in turn integrally made with the latter, and are extended parallel to each other towards the first main body 5 starting from the second front face 6A.

The two pairs of rods 111 and 112 are at least partially mutually engaged in a shape relationship in order to guide the movement of the two main bodies 5, 6 with a single degree of freedom in the aforesaid longitudinal direction Y.

More in detail, the two pairs of rods 111, 112 are telescopically inserted inside each other. For example, the first pair of rods 111 are of female type, each with longitudinal cavity at whose interior the rods of male type of the second pair of rods 112 are inserted in a shape relationship, such rods 112 having slightly smaller section with respect to the female rods 111 in order to slidably enter into the longitudinal cavities of the female rods 111 with minimal clearance.

Preferably, the latter rods of female type 111 are transversely placed more externally than the rods of male type 112 in the direction orthogonal to the advancement direction Y of the main bodies 5, 6.

In addition, the rods of female type 111 preferably have C-shaped cross section with facing longitudinal internal concavities. Advantageously, the concavities of the female rods 111 are circumferentially extended by an angle greater than 180° in order to retain the male rods 112 constrained at their interior, also with respect to shifts transverse to the advancement direction Y of the main bodies 5, 6 and lying in the plane of the rods 111, 112.

The rods of the two pairs of rods 111, 112 project from the relative first and second front face 5A, 6A but are also preferably extended on the two lateral sides of the two main bodies 5, 6. More particularly, the two female rods 111 define two corresponding tubular cavities at the two sides of the first main body 5 while the two male rods 112 define two corresponding rails or lobes with convexities directed transversely outward, and counter-shaped with respect to the facing concavities directed towards the interior of the female rods 111.

The two main bodies 5 and 6 are controlled to be moved by the rotation of the actuation head 3 in the first rotation direction between the collected or minimum expansion position, in which the rods of the pair of male rods 112 are substantially entirely inserted in the pair of female rods 111, and an expanded or maximum expansion position, in which the rods of the pair of male rods 112 penetrate into the cavities of the female rods 111 only for a limited terminal portion thereof.

Preferably, in the collected position, the free ends of the female 111 and male 112 rods reach close to, or even flush with, the first and second rear face 5B, 6B respectively of the two main bodies 5 and 6.

In accordance with the embodiment illustrated in FIGS. 15, 16, 19-21, 24, the guide means 9 comprise only one pair of slidable rods 113, which are slidably inserted in opposite, aligned through holes obtained in the main bodies 5, 6. According to such embodiment, the rods are advantageously provided, in a median section thereof, with two opposite cavities 70, in which a peripheral portion of the actuation head 3 is inserted in to keep the pair of rods centered in intermediate position between the main bodies 5, 6 during the actuation of the actuator element. In accordance with this embodiment, in fact, the slidable rods 113 remain stopped and constrained to the head 3 while the main bodies 5, 6 slide with respect thereto, being unthreaded from the slidable rods 113 through the through holes.

In accordance with the embodiments of FIGS. 19-21, 24, only one slidable rod 113 may be provided.

The actuation head 3 is advantageously substantially cylindrical, and is provided, in a per se known manner, with a plurality of first holes 50 with radial extension, circumferentially arranged in an equidistant manner, within which a wrench (not illustrated since of per se known type) can be inserted in order to impart a rotation to the head 3 aimed to adjust the expansion of the expander 1 through its arms 10, 11 on the palate arch. Preferably, there are four such first holes 50 arranged at an angle of 90 degrees from each other.

The actuation head 3 is housed in a seat 14 delimited in the direction transverse to the extension direction Y, between the mutually engaged rods of the two pairs of rods 111, 112 (i.e. in particular between one coupling of male/female rods and the next coupling of male/female rods), and in the direction of the extension Y, between the first and second front face 5A, 6A of the two main bodies 5, 6.

Advantageously, the insertion openings 101A' of each shaped seat 101 are provided (in accordance with the embodiments of FIGS. 1-16,19-21,24) at the first front face 5A and at the second front face 6A of the two main bodies 5, 6.

The shaped seat 101 of the latter is provided with at least one passage opening 102, which is traversed by the corresponding first or second arm 10, 11.

In the case of the embodiments of the figures in accordance with the embodiments of FIGS. 1-16,19-21,24, the passage opening 102 is obtained at the first and second rear face 5B and 6B, i.e. on the opposite side of the main body 5, 6 according to the longitudinal direction Y.

In accordance with such embodiment, the passage opening 102 has narrow cross section, substantially equal to that of the corresponding first and second arm 10, 11 but less than that of the enlarged portion 101A.

In addition, if two support arms 10, 11 are provided for each main body 5, 6, the passage openings 102 can be two separate openings, as is for example indicated in the embodiment of FIGS. 1-16.

In this case, an end stop 103 will be provided that is susceptible of receiving, in abutment, the transversely projecting portion 10A', 11A' of the support arms 10, 11.

The shaped seat 101 in this case will thus comprise an enlarged portion 101A for the housing of the U-shaped transversely projecting connector portion indicated with 10A', 11A', from which two cylindrical seats depart for the passage of the connection portions 10A, 11A of the support arms 10, 11 divided from each other by a separation rib that terminates in the enlarged portion 101A with the end stop 103.

Advantageously, in this case, the two arms 10 or 11 associated with the single main body 5, 6 can be connected to each other by a U-shaped connector portion. The latter will therefore act for both arms 10 or 11 of the body 5 or 6 as transversely projecting portion 10A', 11A', which will thus be housed in the enlarged portion 101A of the shaped seat 101.

In accordance with such embodiment illustrated in FIGS. 1-16, therefore, the insertion opening 101A' placed on the first front face 5A will be sized for receiving such U-shaped connector portion, while the two arms 10 or 11 which depart parallel from such U-shaped will be housed in two cylindrical seats that terminate on the rear face 5B or 6B with two separate passage openings 102.

Figure 26:
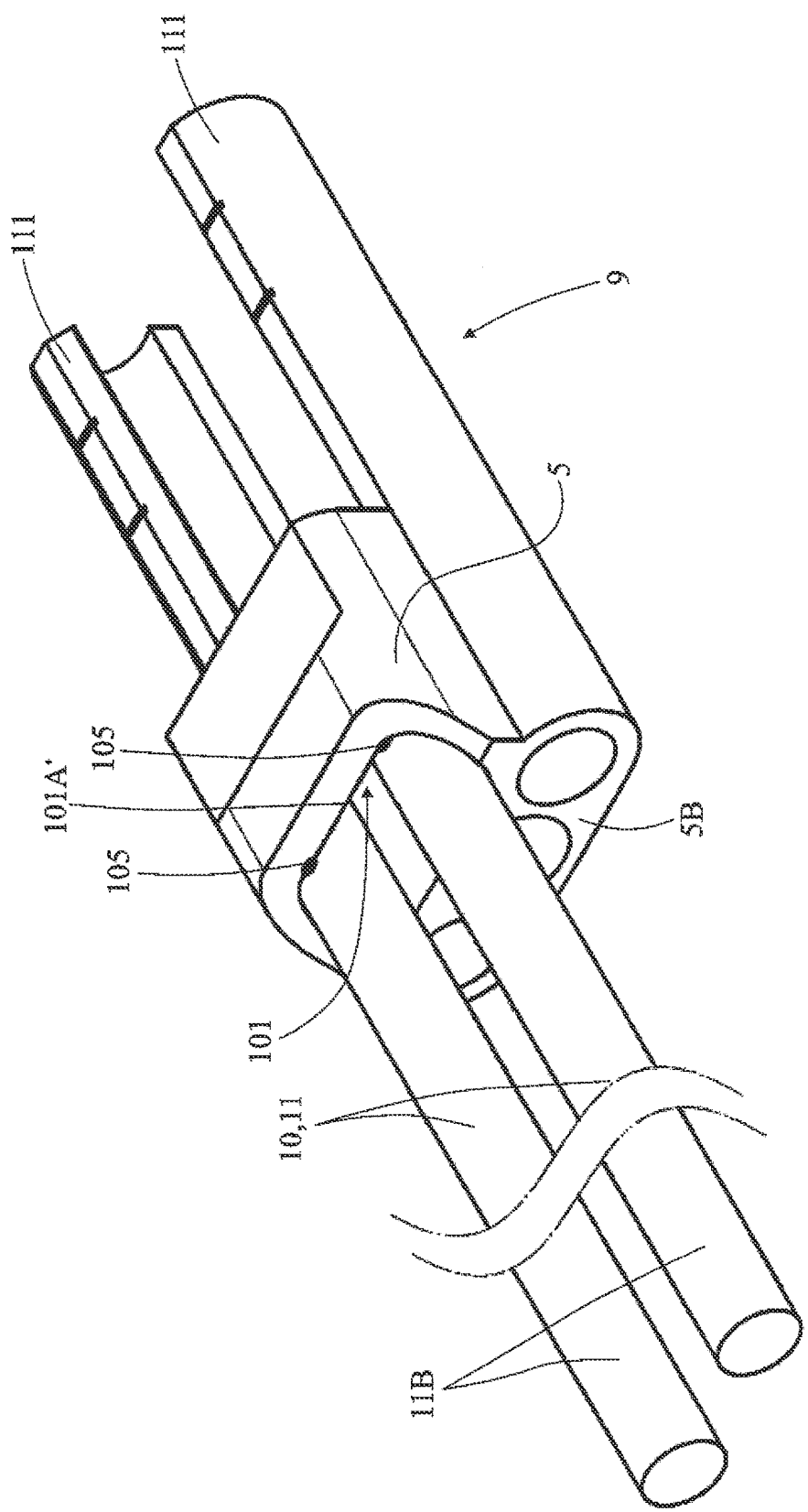
FIG. 26 shows a perspective view of a detail of a further variant of the palatal expander relative to a main body, with the two support arms housed in a provided shaped seat of the same main body with blind pocket shape.
Figure 27:
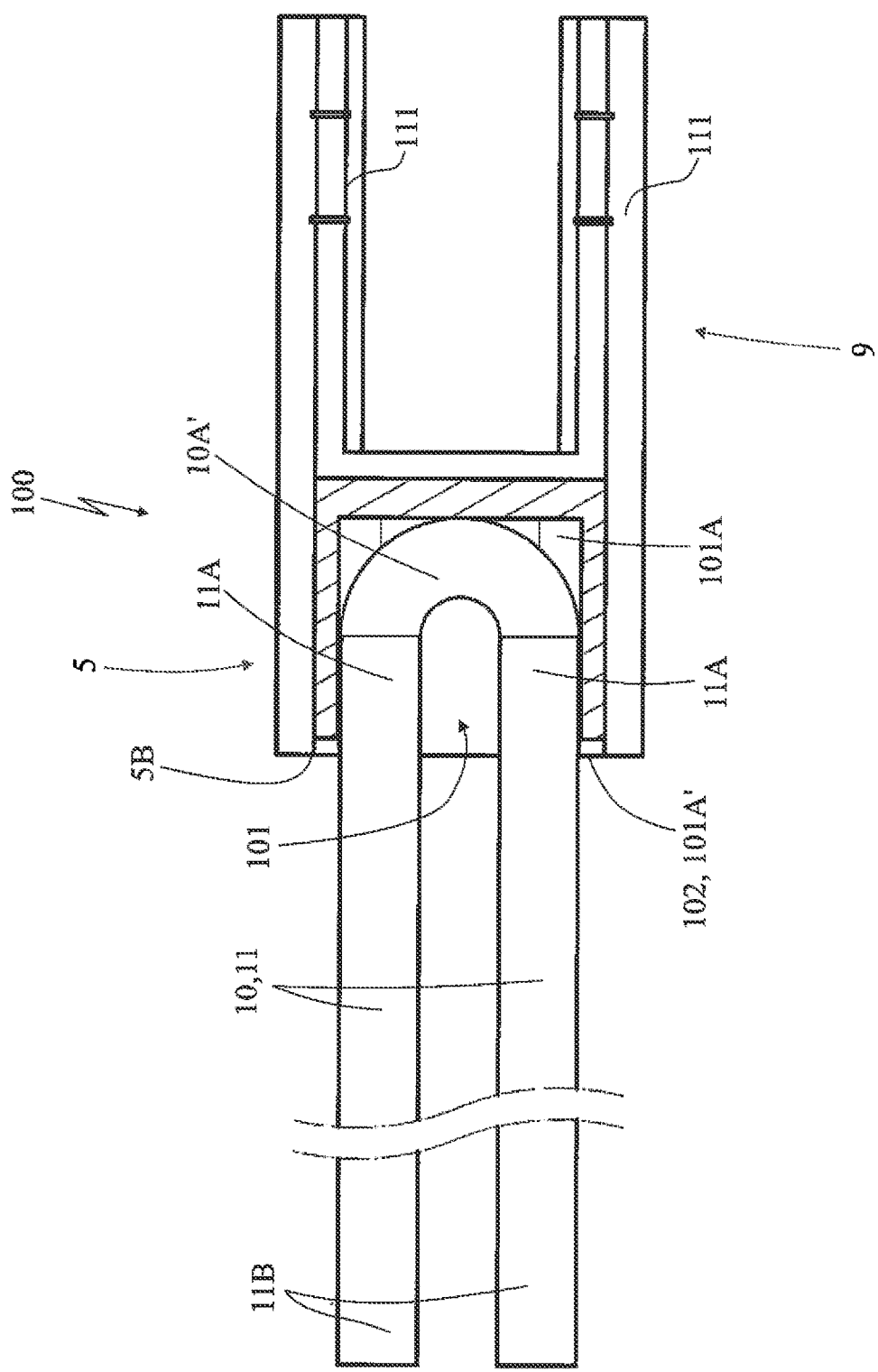
FIG. 27 shows a top view of the main body of FIG. 26, in section in order to better illustrate the blind pocket shape of the shaped seat.

Otherwise, in accordance with the embodiment illustrated in FIGS. 26, 27, the shaped seat 101 of the first and second main body 5, 6 is shaped as a blind pocket with a single insertion and simultaneous passage opening provided on the first and on the second rear face 5B, 6B of the two main bodies 5, 6, which acts as insertion opening 101A' and as passage opening 102 for the arms 10, 11.

In this case, such insertion and passage opening 101A', 102 will have to be sized for the insertion of the transversely projecting portion 10A', 11A'.

In the case illustrated in FIGS. 26, 27, in which the transversely projecting portion 10A', 11A' also acts as a connector for the two support arms 10, 11, the latter will then be extended, traversing through the same insertion opening 101A', without a calibrated passage being provided for.

The shaped seat 101 with blind pocket form on the rear face 5B, 6B of the main bodies 5, 6 is simpler to make than the preceding variants. In addition, once the rapid palatal expander 1 is being used, it is subjected to thrust forces directed towards the bottom of the blind seat; thus ensures that—for the seal of the arms within the main body—two small weld projections 105 are sufficient.

In accordance with one possible embodiment variant, particularly easy to produce, the transversely projecting portion 10A', 11A' of the arms 10, 11 can be obtained with at least one bend of the connection portion in the direction orthogonal to the extension axis of the first and second support arm 10, 11, for example in order to confer a J-shaped (FIGS. 18A, 18B, 19) or L-shaped (FIGS. 17A, 17B) form to such portion, and thus with a terminal appendage susceptible of making that non-aligned, transversely projecting portion 10A', 11A', which—not having cylindrical symmetry—cannot rotate in the shaped seat 101 so to transmit the torsional stresses to the main body 5, 6.

In accordance with the embodiment of the invention illustrated in FIG. 22, two arms 10, 11 will be provided, connected by a transverse connector element also without having any particular interruption with the two arms as in the case of the U-shaped connector. In this case, such transversely projecting connector portion 10A', 11A' can also be obtained with a separate element fixed at one end to the two arms 10, 11.

Figure 25:
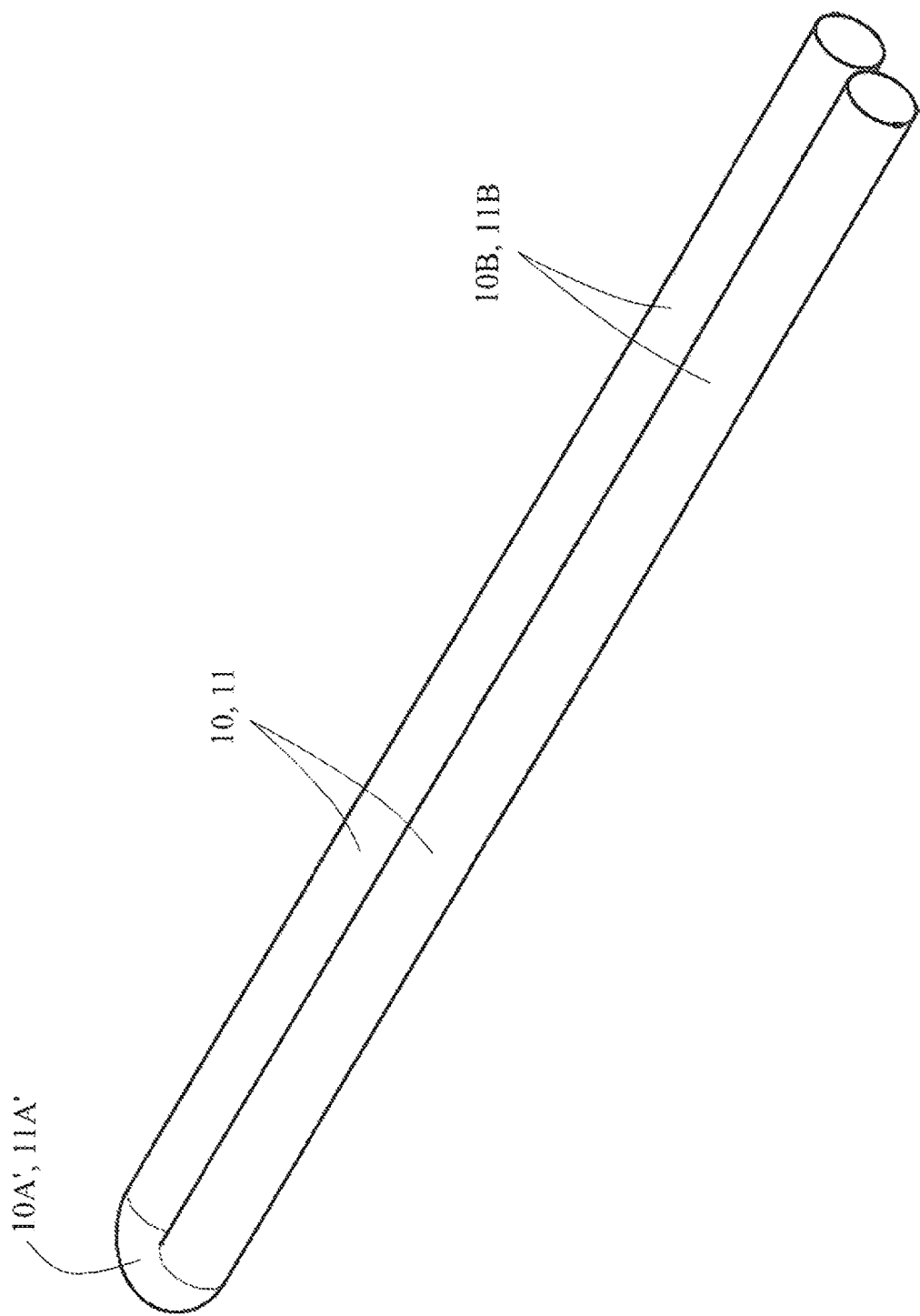
FIG. 25 shows a perspective view of a detail of a variant of the palatal expander relative to two support arms, parallel and brought close, held together by a U-shaped transverse joint portion.

In accordance with the embodiment of the invention illustrated in FIG. 25, two arms 10, 11 are provided that are connected by a transverse U-shaped connector element having interruption with the two arms and integrally obtained therewith by means of simple 180 degree bending. With respect to the variant of FIGS. 1-14, the two support arms 10, 11 are nearly in contact with each other. This necessarily requires a greater deformation thereof during modeling, but in compensation there is the advantage of a reduction in the width bulk of the palate expander 1.

Figure 24:
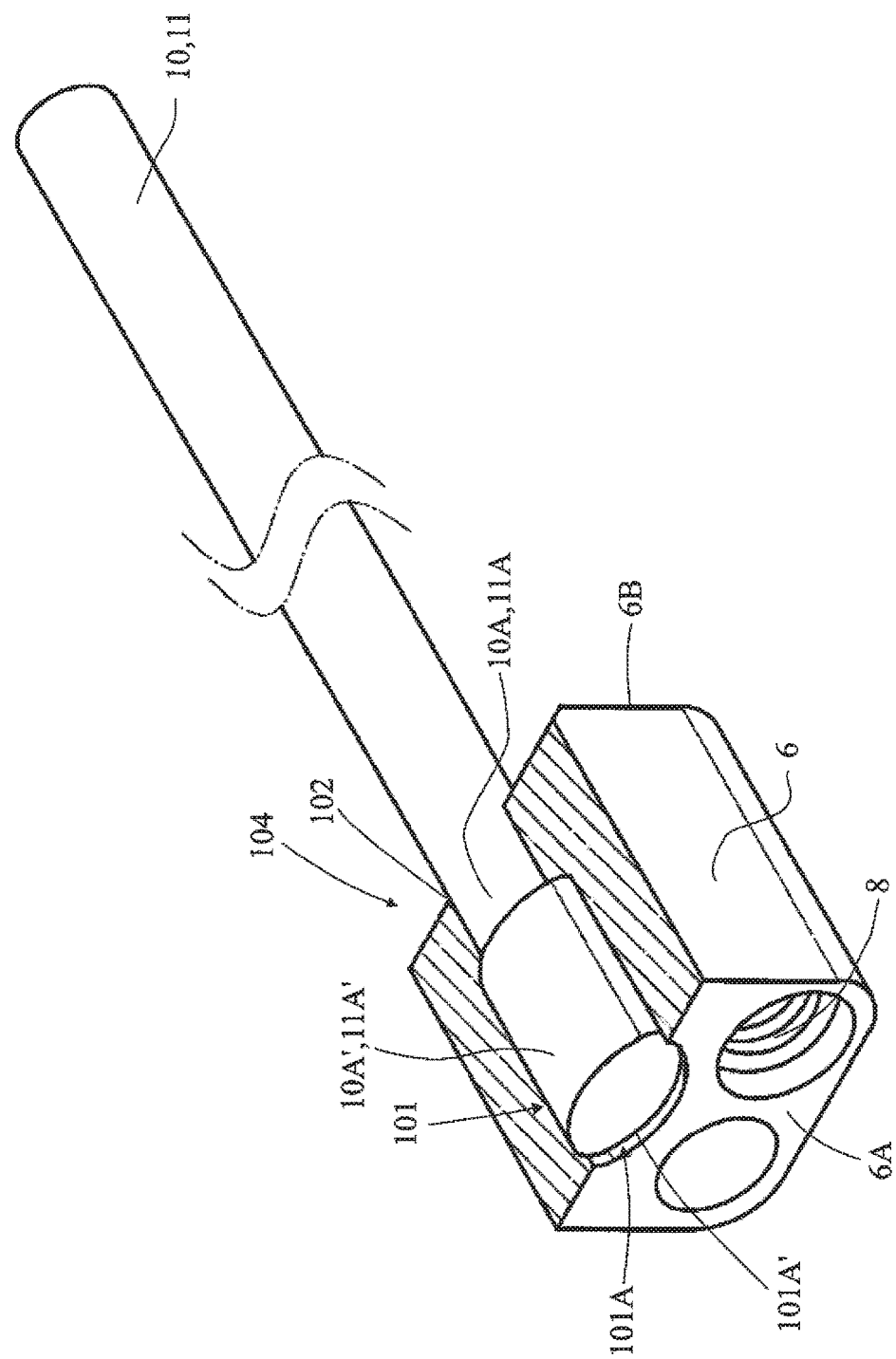
FIG. 24 shows an embodiment variant of the palatal expander illustrated only in part, with a screw provided and only one guide rod fixed to a first main body, illustrated partially in section and susceptible of sliding in an opposite second main body, not illustrated, and with a shaped seat provided for housing a single support body with enlarged head according the embodiment variant of FIG. 23.

In accordance with a further embodiment of the invention illustrated in FIGS. 23, 24, the transversely projecting portion 10A', 11A' of the connection portion can be obtained with a head 104 that is enlarged with respect to the thread-like extension of the remaining part of the arm 10, 11, wherein such enlargement does not have cylindrical symmetry. Advantageously, such enlarged head 104 can be obtained by means of compression of the end of the support arm 10, 11, thus forming two opposite wings with main extension on a plane. In this case, it can be assumed to obtain the enlarged head by crushing one end of the wire that constitutes the arm and obtaining the enlarged head with oval shape (square, rectangular, or the like); of course, this occurs while providing for a correspondingly counter-shaped seat on the main body. The advantage of this variant is tied to the fact that there is less bulk, which can also allow making the shaped seat 101 for the support arm 10, 11 in other zones of the main body 5, 6 (e.g. on the side of the main bodies 5, 6).

The form engagement between the enlarged portion 101A of the shaped seat 101 and the transversely projecting portion 10A', 11A' of the first and second support arm 10, 11 ensures the seal with respect to the torsional stresses; at this point, all that remains is to prevent the unthreading of the arms from the shaped seat 101.

For such purpose, the abovementioned anchorage elements 100 are provided, which will substantially only have the purpose of preventing the unthreading of the arms from the shaped seat 101. In particular, such elements will not have to resist shear stresses nor will they have to generally oppose forces aimed to separate the arms 10, 11 from the main bodies 5, 6 except in the case in which the arms are stretched to exit from the insertion opening 101A'.

The anchorage elements 100 are advantageously obtained by means of at least one weld 105 made between the edge of the passage opening 102 and the external surface of the corresponding first and second arm 10, 11.

Figure 13:
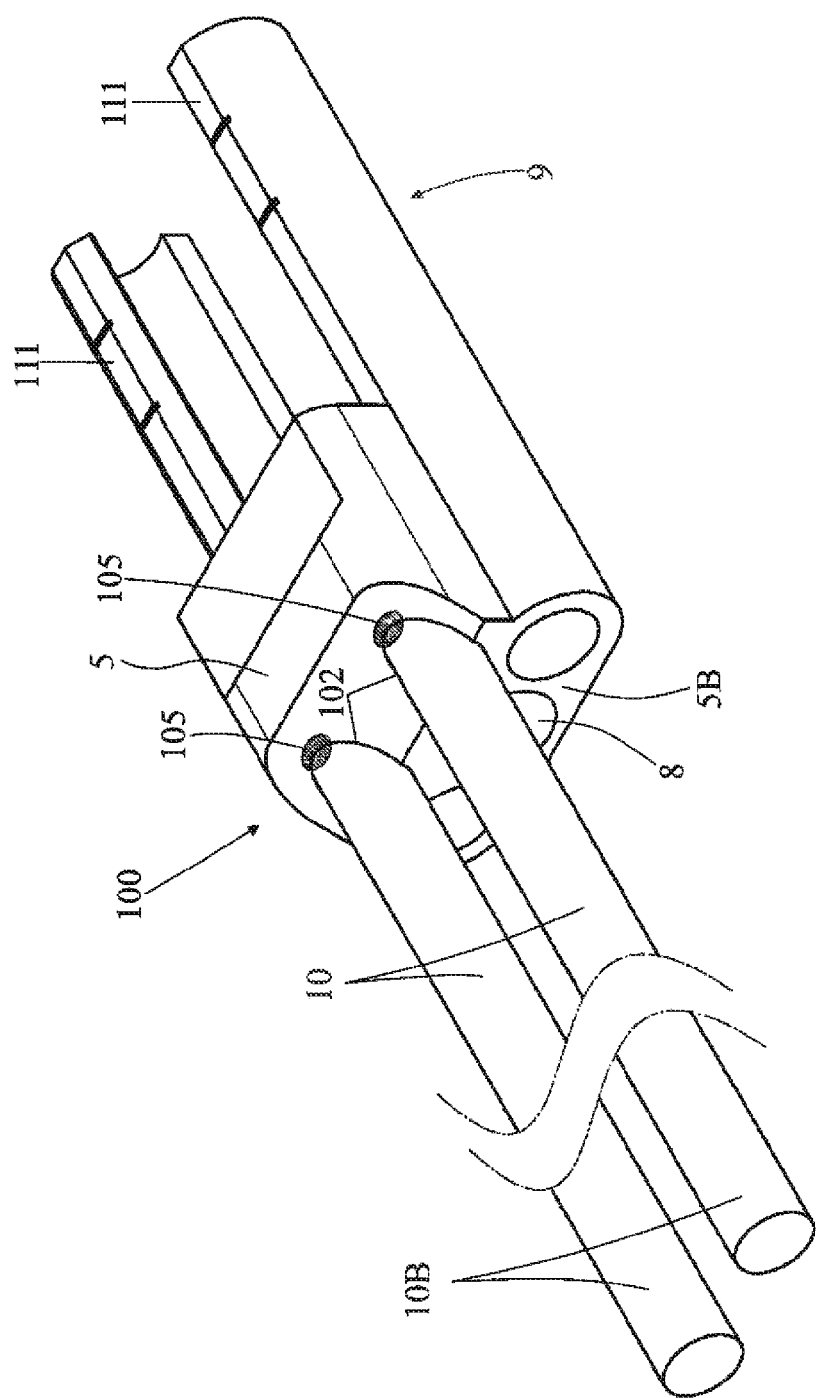
FIG. 13 shows a perspective view of the main body of FIG. 11, no longer in section, with the two support arms housed in a provided shaped seat of the same main body and fixed thereto by means of welding.

In FIGS. 13 and 26, two embodiments are illustrated in which welds 105 are positioned.

Figure 14:
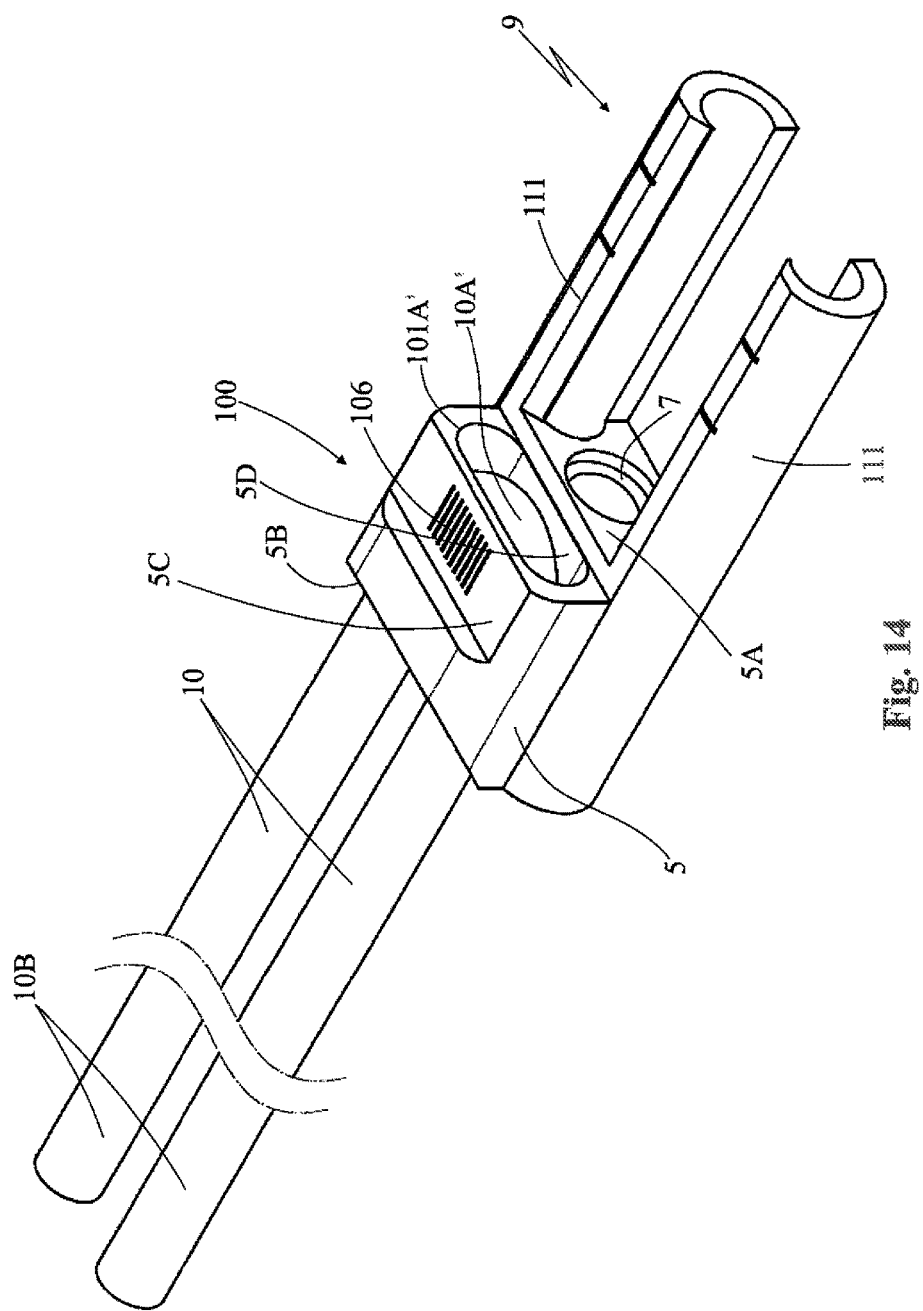
FIG. 14 shows a perspective view of the main body of FIG. 11, no longer in section, with the two support arms housed in a provided shaped seat of the same main body and fixed thereto by means of plastic deformation.
Figure 15:
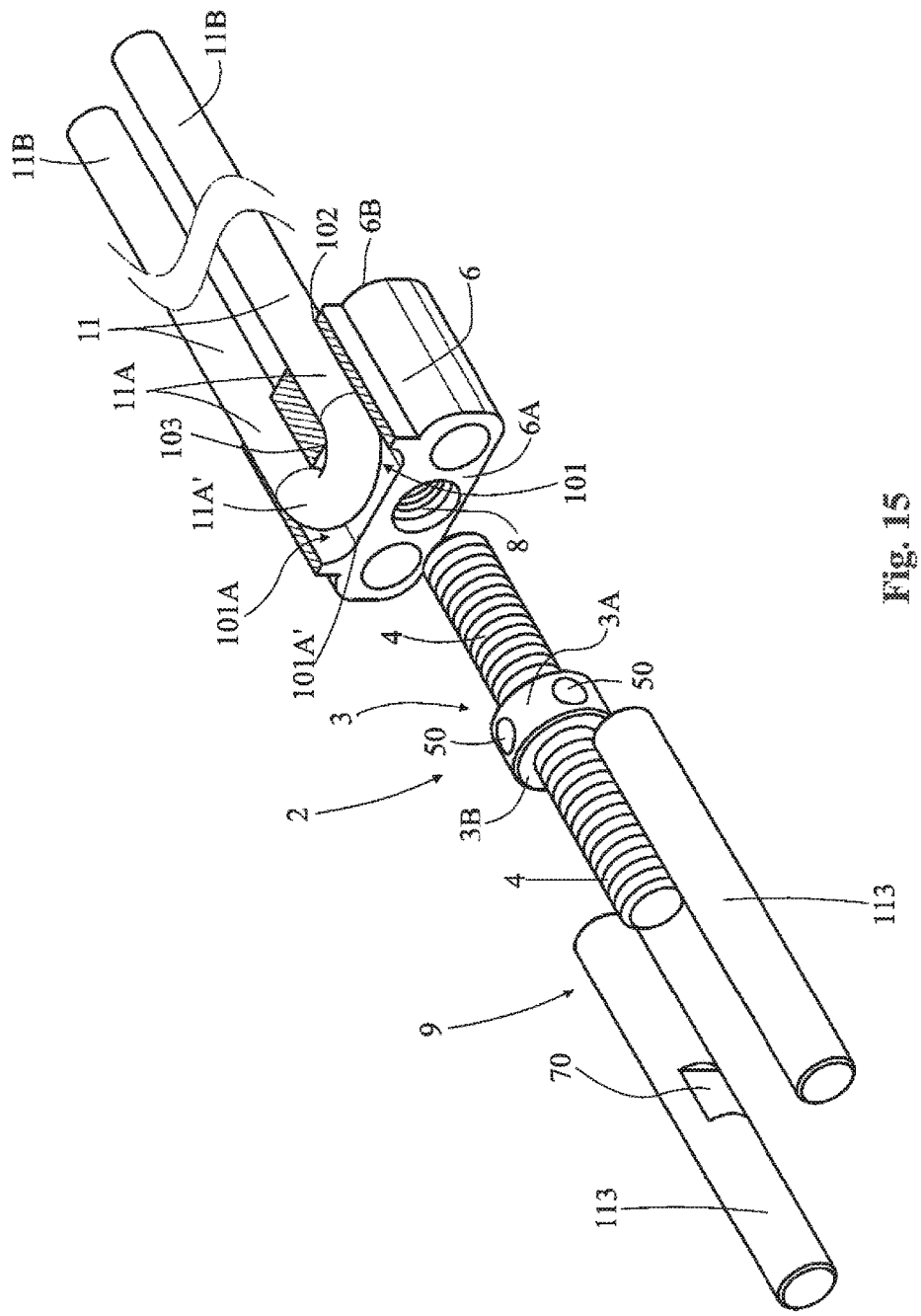
FIG. 15 shows an exploded view of an embodiment variant of the palatal expander according to the present invention, illustrated only in part with two guide rods fixable to a first main body illustrated in section and susceptible of sliding in an opposite second main body, not illustrated.
Figure 20A:
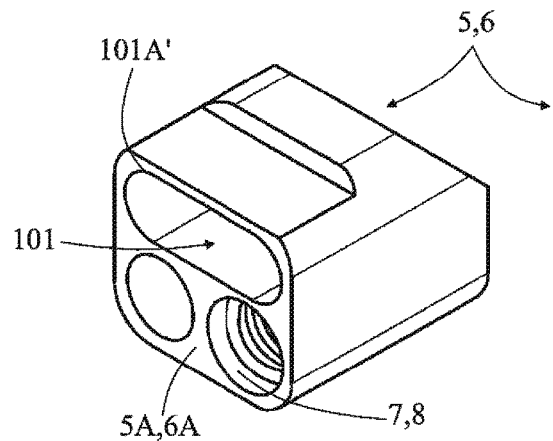
FIGS. 20A and 20B show two different perspective views of an enlarged detail of the palatal expander of FIG. 19 relative to a main body with screw and only one guide pin.
Figure 20B:
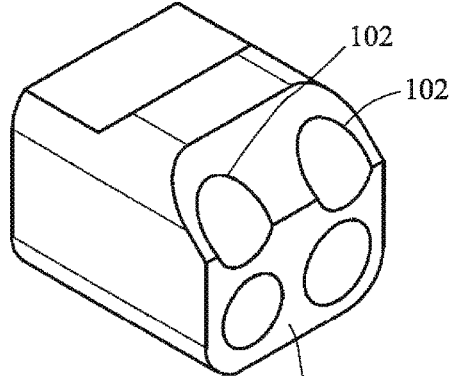
Figure 19:
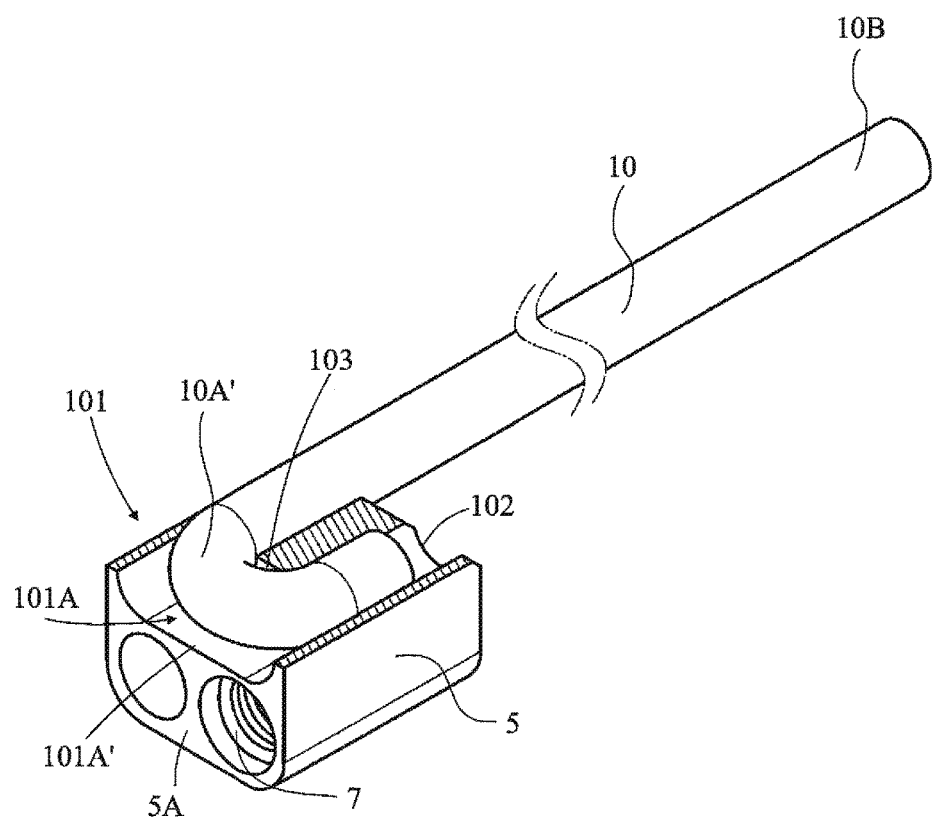
FIG. 19 shows an embodiment variant of the palatal expander illustrated only in part, with a screw provided and only one guide rod fixed to a first main body, illustrated partially in section and susceptible of sliding in an opposite second main body, not illustrated, and with a shaped seat provided for housing a single J-shaped support body according to the embodiment variant of FIGS. 18A and 18B.

Otherwise, in accordance with the embodiment of FIG. 14, the anchorage elements 100 can be obtained with a deformed portion 106 of the first and second main body 5, 6, at the enlarged portion 101A of the shaped seat 101.

Such deformed portion 106 is engaged in retention relationship with the transversely projecting portion 10A', 11A' of the two arms 10, 11 and can be advantageously obtained by means of a cold mold punching.

Of course, the anchorage elements 100 can be made by means of further mechanical selections, without departing from the scope of the present patent, such as by means of an engagement via interference of the transversely projecting portion 10A', 11A' of the first and second enlarged arm 101A in the shaped seat 101.

Also forming an object of the present invention is a method for making a rapid palatal expander, in particular according to the above-described characteristics; for the sake of descriptive simplicity, the same reference numbers and nomenclature will be maintained hereinbelow.

The aforesaid method, according to the idea underlying the present invention, provides for the following operations.

A step is provided for inserting the connection portion 10A, 10B of the arms 10, 11 in the shaped seat 101 until the transversely projecting portion 10A', 11A' is engaged in a shape relationship in the enlarged portion 101A.

Once such final position is reached, with the transversely projecting portion 10A', 11A' housed in the enlarged portion 101A, a step follows for locking the support arms 10, 11 to the main bodies 5, 6.

The insertion step can occur by introducing the terminal portions 10B, 11B of the two support arms 10, 11 through the respective insertion openings 101A' obtained in the corresponding first and second front face 5A, 6A as well as, in succession, through the passage openings 102 of the first rear face 5B and second rear face 6B of the same main bodies 5, 6.

Such insertion operation will continue until the transversely projecting portion 10A', 11A' is brought into the enlarged portion 101A with the support arms 10, 11 arranged to traverse the passage openings 102.

Preferably, the insertion step occurs until the transversely projecting portion 10A', 11A' is abutted against an end stop 103 provided in the shaped seat 101.

Advantageously, according to the embodiment illustrated in FIGS. 26 and 27, the insertion step occurs by introducing the transversely projecting portion 10A' of the first support arm 10 and the transversely projecting portion 11A' of the second support arm 11 respectively through the insertion opening 101A' obtained in the first rear face 5B of the first main body 5 and through the insertion opening 101A' obtained in the second rear face 6B of the second main body 6, until the transversely projecting portion 10A', 11A' is brought to be housed in the corresponding enlarged portion 101A with the corresponding support arms 10, 11 arranged to traverse the corresponding insertion opening 101A'. Preferably, in such insertion step, the transversely projecting portion 10A', 11A' is abutted against the blind bottom of the corresponding shaped seat 101 shaped as a blind pocket.

The abovementioned locking step can be obtained by means of a weld 105 made between the edge of the passage opening 102 and the external surface of the corresponding first and second arm 10, 11, i.e. by means of a deformation of the first and second main body 5, 6, in particular by means of a cold punching operation, at the enlarged portion 101A of the shaped seat 101.

The aforesaid deformation will cause an engagement of the deformed portion 106 in retention relationship with the transversely projecting portion 10A', 11A' of the connection portion 10A, 11A of the two arms 10, 11.

The invention claimed is:

1. A rapid palatal expander which comprises:
 a first and a second main body, each of which provided with a corresponding external surface;
 an actuator element mechanically engaged with said first and second main body and actuatable to move said first and second main body relative to each other along a longitudinal slide direction;
 at least one first and one second support arm, each provided with an elongated extension that extends at least partially along a corresponding extension axis parallel to said longitudinal slide direction, wherein each said first and second support arm is provided with a corresponding connection portion which is mechanically fixed respectively to said first and second main body by means of respective anchorage elements, and wherein said first and second support arm are provided with corresponding terminal portions which are susceptible of imparting corrective actions on opposite sides of a dental arch of a patient;
 wherein the connection portion of each said first and second support arm comprises a transversely projecting portion, which extends transversely with respect to the extension axis of the corresponding said first and second support arm;
 wherein said first and second main body each comprise a shaped seat provided with an enlarged portion countershaped with respect to the corresponding said transversely projecting portion, each said enlarged portion being engaged with the corresponding said transversely projecting portion by virtue of the shape of each said enlarged portion and the shape of each said transversely projecting portion, the enlarged portion of each said shaped seat being extended with an insertion opening on the external surface of the corresponding said first and second main body;
 wherein the enlarged portion of each said shaped seat encloses the transversely projecting portion of the connection portion of the corresponding first and second support arm around the extension axis of said first and second support arm sufficient for preventing the rotation of each said transversely projecting portion in each said enlarged portion;
 wherein the external surface of said first main body extends outside the shaped seat of said first main body and is provided with a first front face;
 wherein the external surface of said second main body extends outside the shaped seat of said second main body and is provided with a second front face facing said first front face;
 wherein the external surface of said first main body is provided with a first rear face oriented in an opposite orientation with respect to said first front face;
 wherein the external surface of said second main body is provided with a second rear face oriented in an opposite orientation with respect to said second front face;
 wherein said first support arm exits the shaped seat of said first main body through said first rear face;
 wherein said second support arm exits the shaped seat of said second main body through said second rear face.

2. The rapid palatal expander according to claim 1,
 wherein the insertion opening of the shaped seat of said first main body and the insertion opening of the shaped seat of said second main body are respectively made on said first front face and on said second front face;
 wherein the shaped seat of said first main body and the shaped seat of said second main body are each provided with at least one passage opening;
 wherein said at least one passage opening of said first main body is made on said first rear face and is crossed by said first support arm;
 wherein said at least one passage opening of said second main body is made on said second rear face and is crossed by said second support arm.

3. The rapid palatal expander according to claim 2, wherein said at least one passage opening of each shaped seat on the respective first rear face and on the respective second rear face has narrow cross section equal to that of the corresponding said first and second support arm and less than that of the insertion opening of the enlarged portion of the corresponding shaped seat.

4. The rapid palatal expander according to claim 1, wherein the enlarged portion of each said first and second main body is provided with at least one passage opening traversed by the corresponding first and second support arm; and
   wherein said anchorage elements comprise at least one weld made between an edge of said at least one passage opening and an external surface of the corresponding said first and second support arm.

5. The rapid palatal expander according to claim 1, wherein said anchorage elements comprise at least one deformation of said first and second main body at the enlarged portion of the corresponding said first and second shaped seat, said at least one deformation being engaged in a retention relationship with the transversely projecting portion of the connection portion of the corresponding first and second support arm.

6. The rapid palatal expander according to claim 1, wherein the transversely projecting portion of said connection portion comprises at least one shaped bend of the corresponding said first and second support arm.

7. The rapid palatal expander according to claim 3, wherein said transversely projecting portion of said first and second support arms is U-shaped, and two said first or second arms passing through two separate passage openings depart from the corresponding said transversely projecting portion.

8. The rapid palatal expander according to claim 1, wherein the shaped seat of said first and second main body has a closed bottom end, and has the insertion opening made on the corresponding said first and second rear face and traversed by the corresponding said first and second support arm.

9. The rapid palatal expander according to claim 1, characterized in that said first and second main body are each provided with an upper wall and with a lower wall,
   wherein the upper wall and the lower wall of said first main body are opposite each other, and the upper wall and the lower wall of said second main body are opposite each other,
   wherein the upper wall and the lower wall of each first and second main body delimit two symmetric parts of the corresponding enlarged portion and are shaped in a manner so as to prevent the rotation within the enlarged portion of the transversely projecting portion of the corresponding said first and second support arm.

10. The rapid palatal expander according to claim 1, wherein the insertion opening of the enlarged portion of said shaped seat has size greater than or equal to the cross section of said transversely projecting portion engaged in said enlarged portion.

* * * * *